(12) United States Patent
Liederman et al.

(10) Patent No.: US 8,076,128 B2
(45) Date of Patent: Dec. 13, 2011

(54) AUTOMATED ANALYZER USING LIGHT DIFFRACTION

(75) Inventors: Adam Liederman, Toronto (CA); Raymond Francis Cracauer, Beulah, CO (US); Rocky Ganske, Acton (CA); Huatang Wu, Scarborough (CA); Sorin Turlea, Cambridge (CA)

(73) Assignee: Axela Inc., Etobicoke, ON (CA)

( * ) Notice: Subject to any disclaimer, the term of this patent is extended or adjusted under 35 U.S.C. 154(b) by 846 days.

(21) Appl. No.: 11/798,034

(22) Filed: May 9, 2007

(65) Prior Publication Data
US 2007/0264707 A1 Nov. 15, 2007

Related U.S. Application Data

(60) Provisional application No. 60/798,719, filed on May 9, 2006.

(51) Int. Cl.
*C12M 1/34* (2006.01)
(52) U.S. Cl. .............. 435/288.7; 435/286.5; 435/287.5; 435/288.5; 427/2.11; 436/518; 436/43
(58) Field of Classification Search ........................ None
See application file for complete search history.

(56) References Cited

U.S. PATENT DOCUMENTS

| 7,008,794 | B2 | 3/2006 | Goh | |
|---|---|---|---|---|
| 2001/0046047 | A1* | 11/2001 | Ryer | 356/328 |
| 2003/0032039 | A1 | 2/2003 | Cunningham | |
| 2004/0096368 | A1* | 5/2004 | Davis et al. | 422/104 |
| 2005/0037485 | A1* | 2/2005 | Rodgers et al. | 435/287.2 |
| 2005/0148063 | A1* | 7/2005 | Cracauer et al. | 435/287.2 |

FOREIGN PATENT DOCUMENTS

CA 2301095 2/1999
WO 2004/108270 6/2004

* cited by examiner

*Primary Examiner* — N. C. Yang
(74) *Attorney, Agent, or Firm* — Lynn C. Schumacher; Hill & Schumacher

(57) ABSTRACT

The present invention provides an automated analyzer system for performing chemical, biochemical or biological assays using changes/no changes in diffraction of light by the presence/absence of analytes which may or may not be present in a sample binding to their analyte specific receptors laid out in a preselected pattern in a disposable sensor. The analyzer is a modular, bench-top instrument that compactly integrates subsystems for sample dispensing, liquid handling, and optical generation of laser light beams and detectors for detecting for diffracted light. An internal processor is included for automating the instrument, and a user interface to provide communication with the operator.

34 Claims, 16 Drawing Sheets

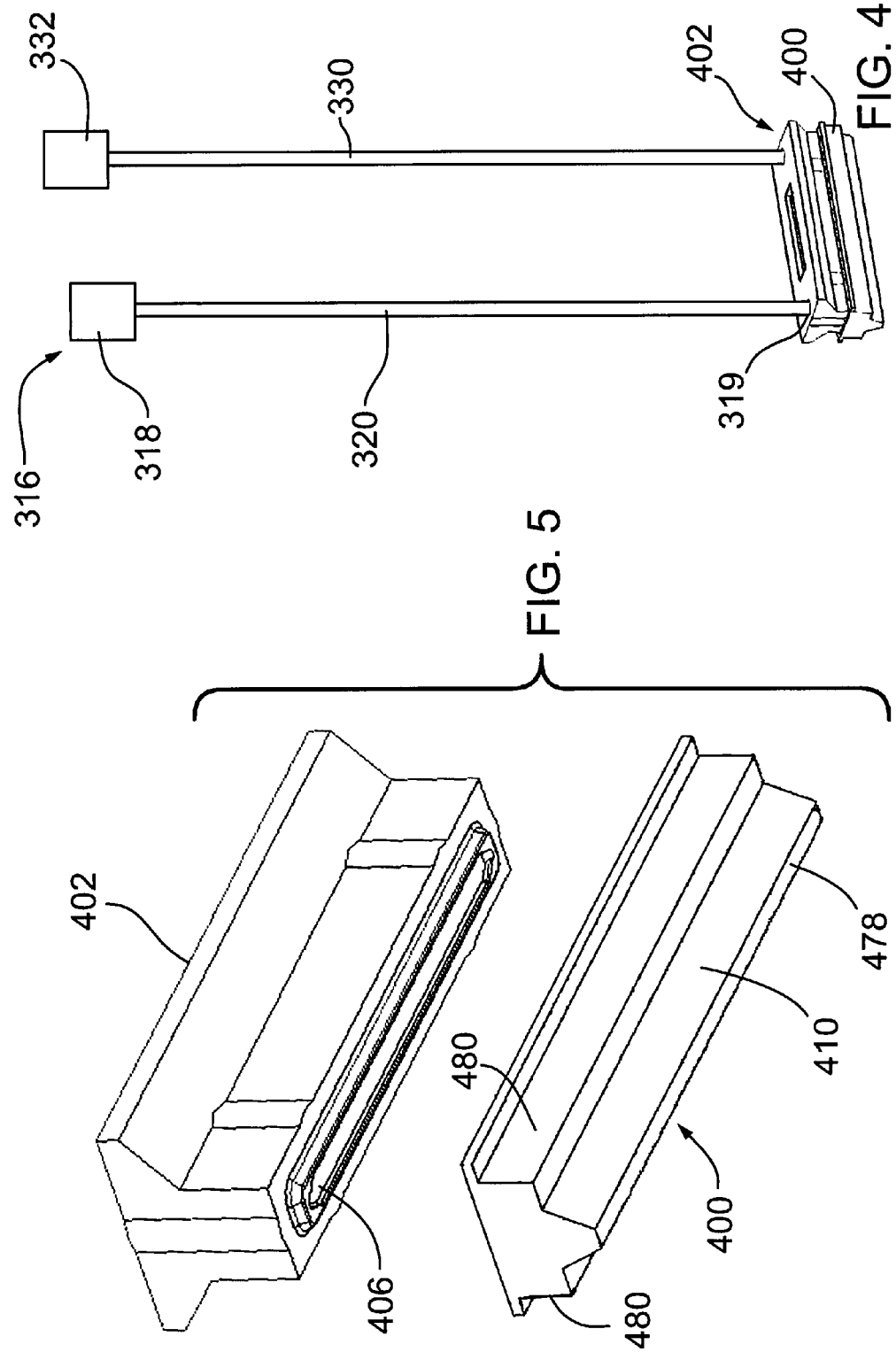

$n_{PROTEIN} = 1.43 = n_R$ $n_{POLYSTYRENE} = 1.58 = n_i$

IN ORDER TO OPERATE IN TIR (TOTAL INTERNAL REFLECTION)

$\theta_{CRITICAL} = ASIN(n_R/n_i) = 65°$

THEREFORE $180° - 65° - 90° = \phi = 25°$

AUTOMATED ANALYZER USING LIGHT DIFFRACTION

CROSS REFERENCE TO RELATED U.S. APPLICATIONS

This patent application relates to, and claims the priority benefit from, U.S. Provisional Patent Application Ser. No. 60/798,719 filed on May 9, 2006, in English, entitled AUTOMATED ANALYZER USING LIGHT DIFFRACTION, and which is incorporated herein by reference in its entirety.

FIELD OF THE INVENTION

The present invention is related to an automated analyzer particularly for applications for analyte detection using diffractive optics technology.

BACKGROUND OF THE INVENTION

Recently, automated analyzers for performing chemical, biological and biochemical assays have become widespread for use by diagnostic & research laboratories for the rapid and reliable detection of analytes in a variety of biological samples. Analyzers are routinely used to perform a wide variety of assays, most of which involve immunoassays where the high affinity and selectivity of an antibody for its antigen is exploited. Many of these systems are based on measurement of emitted light such as chemiluminescence caused by reactions in the assay.

For example, in many instances, it is desirable to determine the presence and the amount of a specific material in solution (the 'medium'). Surface-based assays rely on the interaction of the material to be assayed (the 'analyte') with a surface that results in a detectable change in any measurable property. For the purpose of this patent application, the term 'analyte' refers to the material to be assayed. Examples of analytes include: an ion; a small molecule; a large molecule or a collection of large molecules such as a protein or DNA; a cell or a collection of cells; an organism such as a bacterium or virus. 'Analyte-specific receptor, or 'recognition element' refers to that complementary element that will preferentially bind its partner analyte. This could include: a molecule or collection of molecules; a biomolecule or collection of biomolecules, such as a protein or DNA; a groove on the substrate that has the complementary geometry and/or interaction. In general, in order to assay for a specific analyte, the surface is modified so as to offer the appropriate chemical interaction.

In immunoassays, for example, one takes advantage of the specificity of the antibody-antigen interaction: A surface can be coated with an antigen in order to assay for the presence of its corresponding antibody in the solution or vice versa. Similarly, a strand of deoxyribonucleic acid (DNA) can be attached to a substrate and used to detect the presence of its complementary strand in solution. In any of these cases, the occurrence of binding of the analyte to its recognition element on the surface, which thus identifies the presence of the specific analyte in solution, is accompanied by a detectable change. For example, the binding can produce a change in the index of refraction at the interfacial layer; this can be detected by ellipsometry or surface plasmon resonance. Alternatively, the bound analyte molecules may emit light; this emission can be collected and detected, as is the case for fluorescence-based sensors. Non-optical signals may also be used, as in the case of radio immunoassays and acoustic wave sensing devices.

Diffraction is a phenomenon that occurs due to the wave nature of light. When light hits an edge or passes through a small aperture, it is scattered in different directions. But light waves can interfere to add (constructively) and subtract (destructively) from each other, so that if light hits a non-random pattern of obstacles, the subsequent constructive and destructive interference will result in a clear and distinct diffraction pattern. A specific example is that of a diffraction grating, which is of uniformly spaced lines, typically prepared by ruling straight, parallel grooves on a surface. Light incident on such a surface produces a pattern of evenly spaced spots of high light intensity. This is called Bragg scattering, and the distance between spots (or 'Bragg scattering peaks') is a unique function of the diffraction pattern and the wavelength of the light source. There is a unique correspondence between a pattern and its diffraction image, although in practice, diffraction is best illustrated by using periodic patterns, because these yield easily recognized diffraction images of clearly defined regions of high and low light intensity.

There is therefore a need for an analyzer which is based on diffraction of light that that offers ease of use, minimal sample handling, low consumable cost and assay versatility in a compact instrument.

SUMMARY OF THE INVENTION

The present invention addresses the need for an automated analyzer for diffraction-based screening of fluids such as liquids for analytes.

An embodiment of an analyzer for performing chemical, biochemical or biological assays using diffraction of light, comprises:

a disposable sensor including at least one sample well and at least one pre-selected pattern of analyte-specific receptors bound to a surface of said at least one sample well;

at least one sensor station for receiving said disposable sensor;

a fluid holding sample container for holding assay fluids used in performing said assays and samples being tested for presence or absence of analytes which bind to said analyte-specific receptors;

a fluid flow and handling system in flow communication with said at least one sensor, sources of said samples and sources of said assay fluids used in performing said assays configured to deliver said samples and fluids to said at least one well in said disposable sensor and said fluid holding sample container, said fluid flow and handling system including fluid pump configured to pump fluids and samples from their respective sources to said disposable sensor, to said fluid holding sample container and to fluid waste containers, said fluid flow and handling system including a fluid dispenser configured to dispense samples and fluids to said fluid holding sample container and to dispense samples and assay fluids from said fluid holding sample container to said at least one sensor;

a robotic manipulator connected to said fluid holding sample container configured to pre-position said fluid holding sample container with respect to said fluid dispenser;

a temperature controller for controlling a temperature of an interior of the analyzer;

an optical system for producing and directing a coherent beam of light toward said at least one sensor station to impinge on said surface of said at least one sample well containing said at least one pre-selected pattern of analyte-specific receptors bound thereto, said optical system including a first optical detector configured to measure diffracted light signals from said at least one pre-selected pattern of analyte-specific receptors;

a scanning mechanism for scanning said coherent beam of light with respect to said at least one sample well containing said at least one pre-selected pattern of analyte-specific receptors bound thereto; and a microprocessor controller connected to said scanning mechanism, said scanning mechanism being configured to scan said coherent light beam across said surface in a controlled manner, and said microprocessor controller being programmed with instructions to scan said coherent light beam across pre-selected portions of said at least one pre-selected pattern of analyte-specific receptors prior to flowing sample containing the analytes into said disposable sensor, and based on qualities of signals received from said pre-selected portions, the microprocessor being programmed with instructions to determine a selected region in said at least one pre-selected pattern of analyte-specific receptors to subsequently monitor said diffracted light signals after sample has been admitted into said disposable vessel;

said microprocessor controller also being connected to
said temperature controller, and programmed to control the temperature controller to control the temperature in said analyzer,
said robotic manipulator, and programmed to pre-position said fluid holding sample container with respect to said fluid dispenser,
said fluid flow and handling system, and programmed to control sample and assay fluid flow routes through said fluid control system,
said optical system, and programmed to control parameters of said coherent light beam, said optical detector being configured to analyze said measured diffracted light signals from said at least one pre-selected pattern of analyte-specific receptors for determining a presence or absence of analytes in said sample based on the presence or absence of a change in diffraction pattern before and after sample has been admitted into said disposable vessel; and
said microprocessor controller including a user interface enabling interaction between the analyzer and an operator.

A further understanding of the functional and advantageous aspects of the invention can be realized by reference to the following detailed description and drawings.

BRIEF DESCRIPTION OF THE DRAWINGS

The invention will be more fully understood from the following detailed description thereof taken in connection with the accompanying drawings, which form a part of this application, and in which:

FIG. 4 shows an assembled view of an embodiment of a disposable sensor according to the present invention;

FIG. 5 shows an exploded view of a part of the disposable sensor shown in FIG. 4;

DETAILED DESCRIPTION OF THE INVENTION

Generally speaking, the systems described herein are directed to an automated analyzer using light diffraction. As required, embodiments of the present invention are disclosed herein. However, the disclosed embodiments are merely exemplary, and it should be understood that the invention may be embodied in many various and alternative forms. The Figures are not to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present invention. For purposes of teaching and not limitation, the illustrated embodiments are directed to an automated analyzer using light diffraction.

As used herein, the term "about", when used in conjunction with ranges of dimensions of particles or other physical properties or characteristics, is meant to cover slight variations that may exist in the upper and lower limits of the ranges of dimensions so as to not exclude embodiments where on average most of the dimensions are satisfied but where statistically dimensions may exist outside this region. It is not the intention to exclude embodiments such as these from the present invention.

Figure 1A:
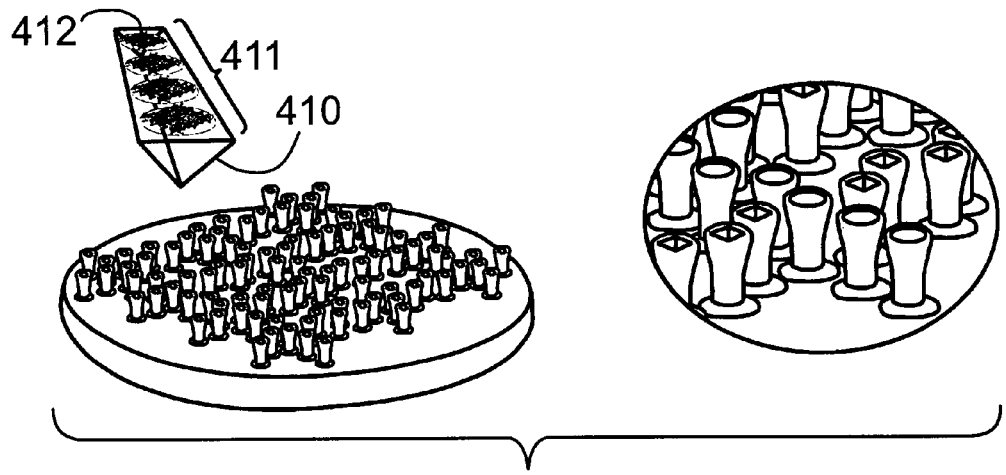
FIG. 1 shows a schematic view of a sensor for analyte-specific detection used in the apparatus of the present invention where A) shows two substrates with analyte-specific receptors, B) shows the interrogation of the receptors with nothing bound, and C) shows the interrogation of the receptors with analyte bound.
Figure 1B:
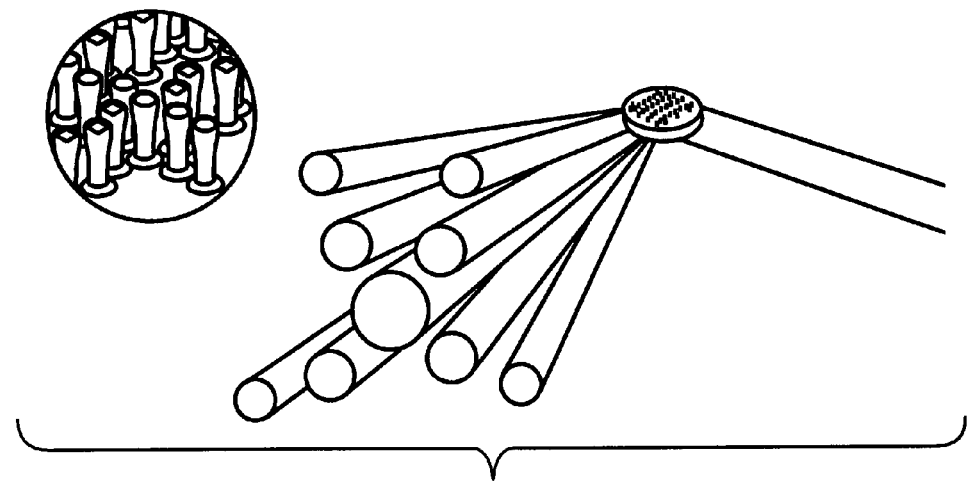
Figure 1C:
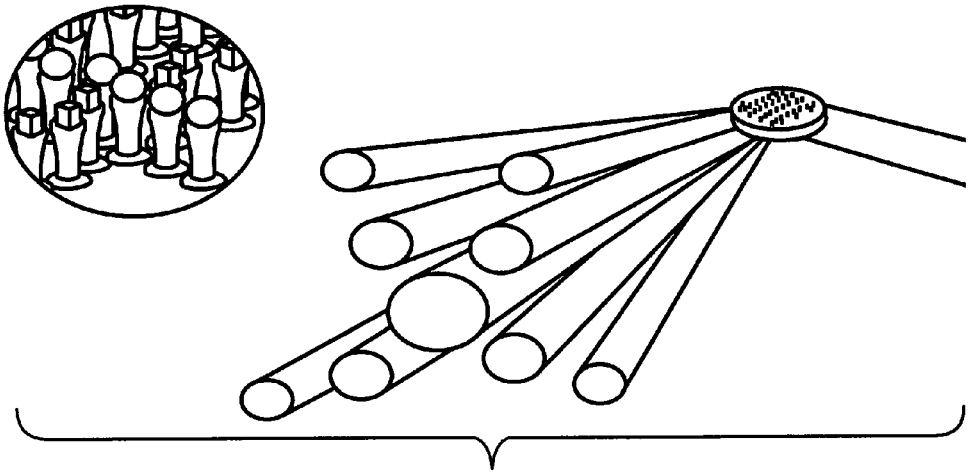

The present invention provides an automated or user operated bench-top instrument intended for use in analyte detection and/or examining binding events using diffractive optics technology which may be used in research or diagnostic applications. Diffraction occurs due to the wave nature of light: when light hits a non-random pattern of obstacles, the resulting constructive and destructive interference will result in a clear diffraction image. Referring to FIG. 1A, an when proteins, antibodies, or other molecules are deposited on a surface in a specific pattern, a diffractive optical element is created that, when interrogated with a laser as in FIG. 1B, diffracts light into diffractive orders. Binding of analyte to the pattern will increase its mean height, thickness, density, and/or a combination thereof, thereby causing a change in the intensity of diffracted light as in FIG. 1C which is different from intensity in FIG. 1B. This technique is not limited to detection of binding events per se but could also include interactions involving dissociation of bound materials, confirmational changes, compositional changes, and/or a combination thereof.

If the pattern is placed on the surface of properly constructed, optically clear prism, light can interrogate the pattern by total internal reflection (TIR), without passing through the sample. Since the technique can be performed in TIR the analyzer does not require clear solutions.

Details of the method of determining the absence or presence of analytes in a sample using changes in diffraction patterns by the analytes binding to their analyte specific receptors is disclosed in U.S. Pat. No. 7,008,794 issued to Goh et al. on Mar. 7, 2006 entitled: Method And Apparatus For Assay For Multiple Analytes, which is incorporated herein in its entirety by reference.

Figure 2:
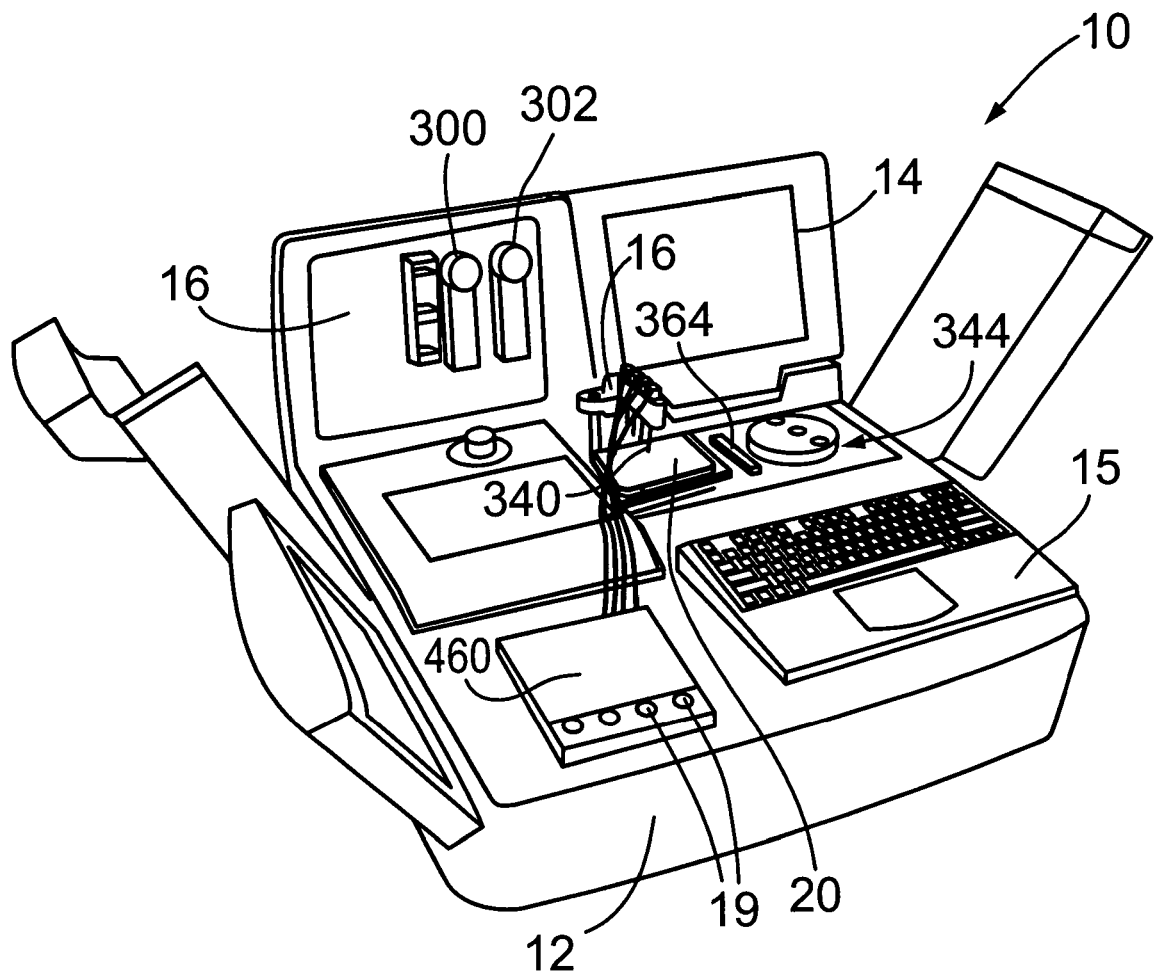
FIG. 2 shows a perspective drawing of the analyzer apparatus.

The instrument constructed in accordance with the present invention is shown generally at 10 in FIG. 2, and includes a housing 12, an integrated computer (microprocessor controller) mounted within the housing 12, in communication with a wireless-keyboard 15, and a monitor 14. The computer is configured with control and processing software which allows coordinated control and monitoring of the fluidic control module 16, the optical subsystem (partially shown at 460), a the two-axis sample handling robot 20, data recording, display, and processing, communication to external devices and networks, and a user interface through which the user can define assay protocols or select and utilize pre-configured assay protocols.

Four sensor stations 19 are shown integrated into the optical subsystem 460, to be described hereinafter, for receiving disposable sensors. The integrated fluidic control module 16 configured to provide delivery of samples, reagents, buffers and the like to the disposable sensors to monitor and subsequently analyze and otherwise conduct assays on samples using a multiplicity of reagents. The two-axis sample handling robot 20 provides walk away automation, sample and reagent loading, accepts microtiter plates or tubes and includes a wash station provided to clean the liquid delivery probes 340.

The instrument will be more comprehensively described beginning with the fluidic control module 16.

Fluid Control Module

The instrument 10 is provided with the automated and integrated fluid control module 16 (FIG. 3A) which is configured to provide delivery of samples, reagents, buffers and the like to sensors 316 to monitor and subsequently analyze and otherwise conduct assays on samples using a multiplicity of reagents.

Figure 3A:
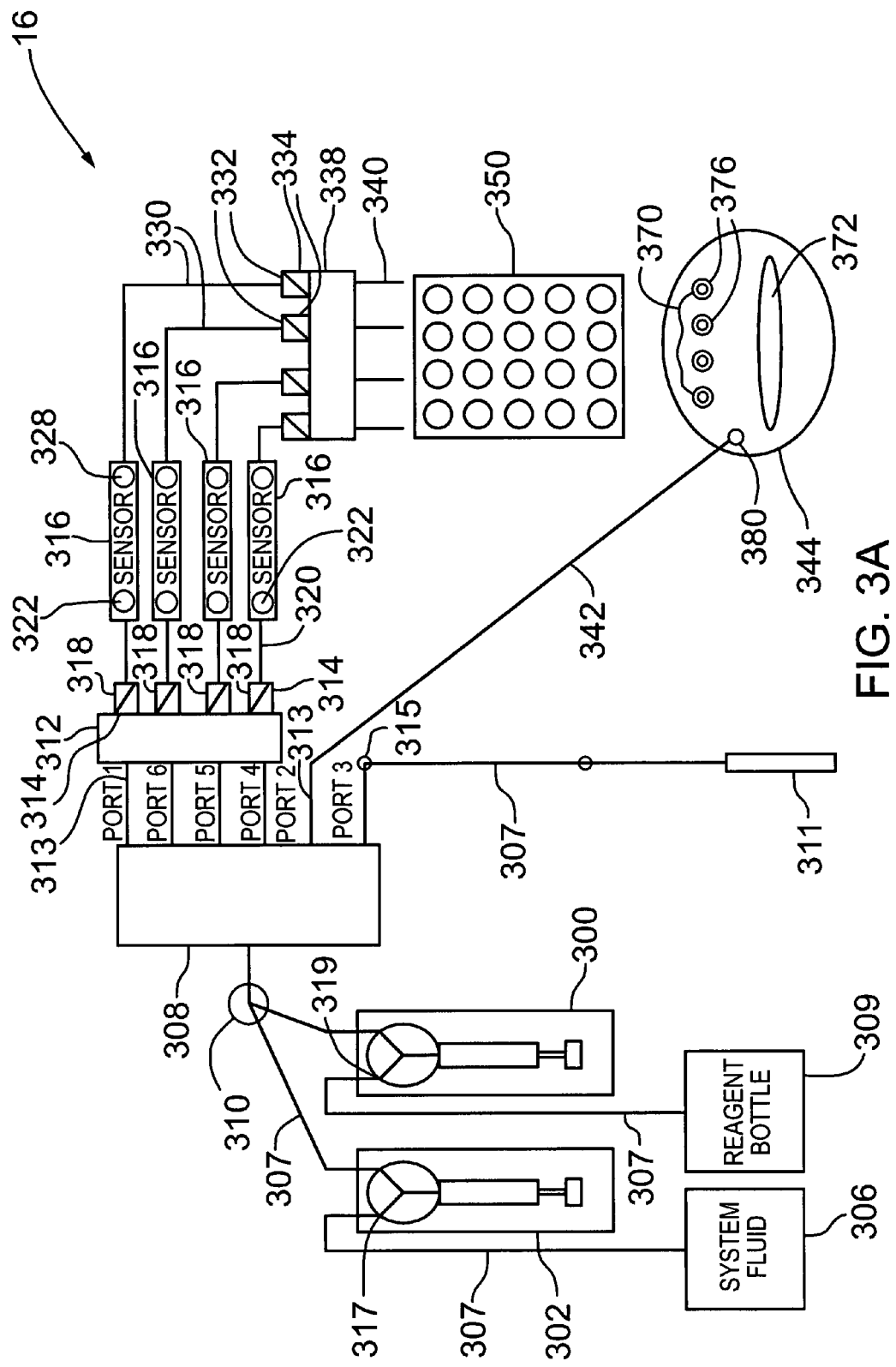
FIG. 3A shows schematic layout of the fluidic control module forming part of the analyzer in FIG. 2.

More particularly FIG. 3A shows a schematic drawing of the fluid control module 16 forming part of the analyzer 10 and includes a fluid or liquid dispensing station having two syringe pumps 300 and 302 both including a multi-port valve. A multi-port rotary valve 308 is connected to the two syringe pumps 300 and 302 through a three-port connector 310. The interconnecting tubing 307 is preferably Teflon tubing with a flangeless ferrule and M6 male nut fitting at each termination. Tubes 313 lead from four ports of the multi-port rotary valve 308 and terminate at the system side of a manifold 312. Three ports 315, 317, and 319 allow for bulk reagents from liquid containers 311, 306 and 309, respectively, to enter the system through valve 308 (from container 311) and through pumps 302 and 300. The sensor side of the manifold 312 is fitted with quick-connect fittings 314, one for each of the four sensors 316, with a format that mates with an injection molded fitting 318 that is glued to a length of PVC tubing (0.060" O.D., 0.020" I.D.) 320 leading to the system side port 322 of each of the sensors 316 where they are permanently connected using glue or some other means of retention, for example, solvent bonding, friction fit, etc.

Figure 7:
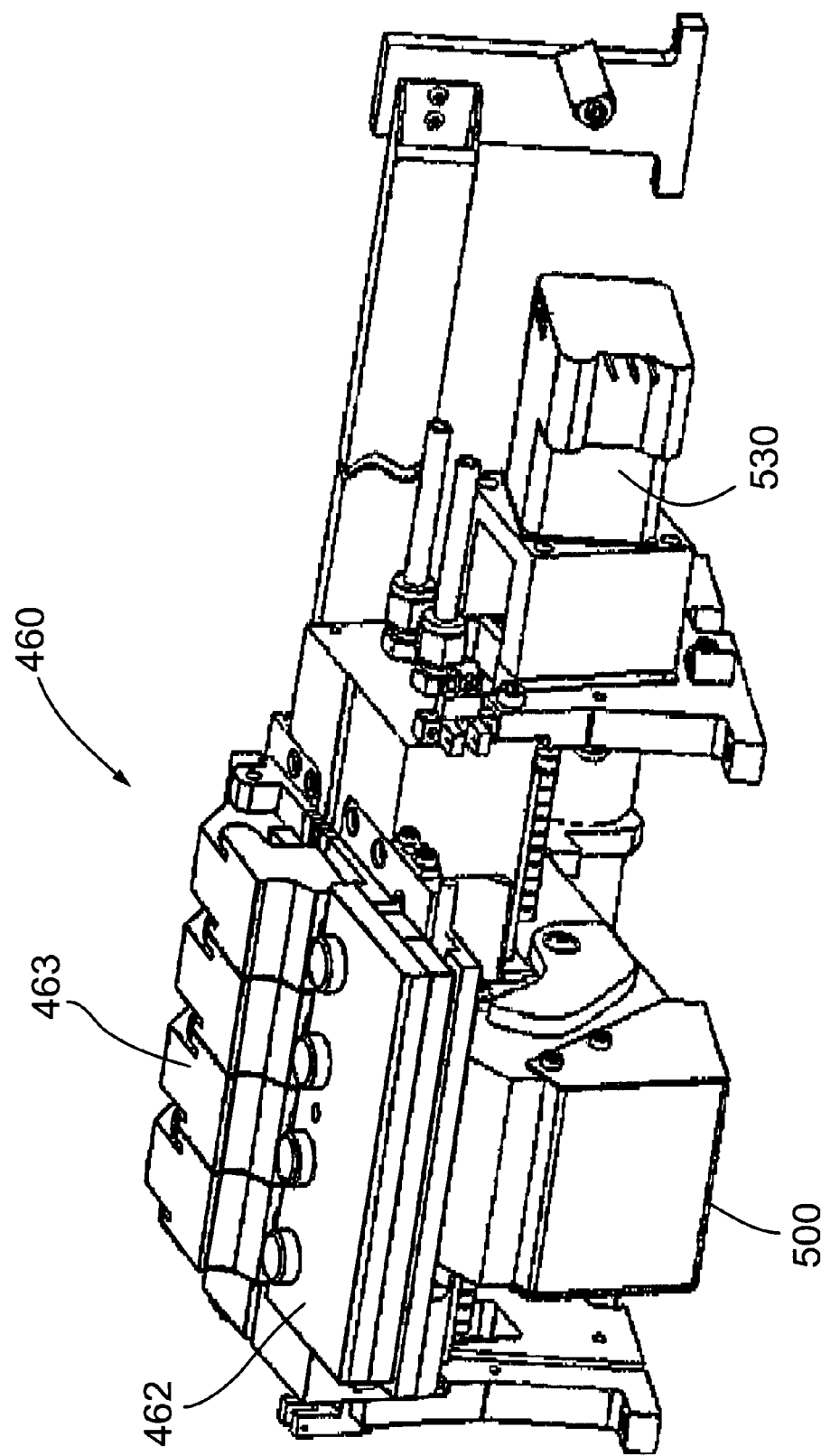
FIG. 7 shows an isometric view of the optics subsystem of the present analyzer.

The sensors 316 include lengths of PVC tubing (0.060" O.D., 0.020" I.D.) 320 and 330 connected to injection molded fittings 318 and 332, respectively. Each injection molded fitting 318 and 332 mate to one quick connect fitting 314 and 334 (partially visible in FIG. 7b) respectively. Quick connect fittings 334 are located on a stationary structure referred to as the arm 338. Each of the four quick connect fittings 334 mounted to the arm 338 make a fluidic coupling to one probe 340 that protrudes beneath the arm 338 and is positioned on a spacing appropriate to access the sample containers 350 which are situated on a two-axis fluid handling robot 20 shown in FIG. 2. It should be noted that probes 340 may be re-usable or disposable.

The entirety of the disposable sensor as shown in FIG. 4 includes the tubes 320 and 330, the injection molded fittings 318 and 332, the upper lid 402, and the patterned prism 400. The instrument 10 can be readily configured to accept alternative constructions of the disposable sensors 316 described hereinafter.

Figure 3B:
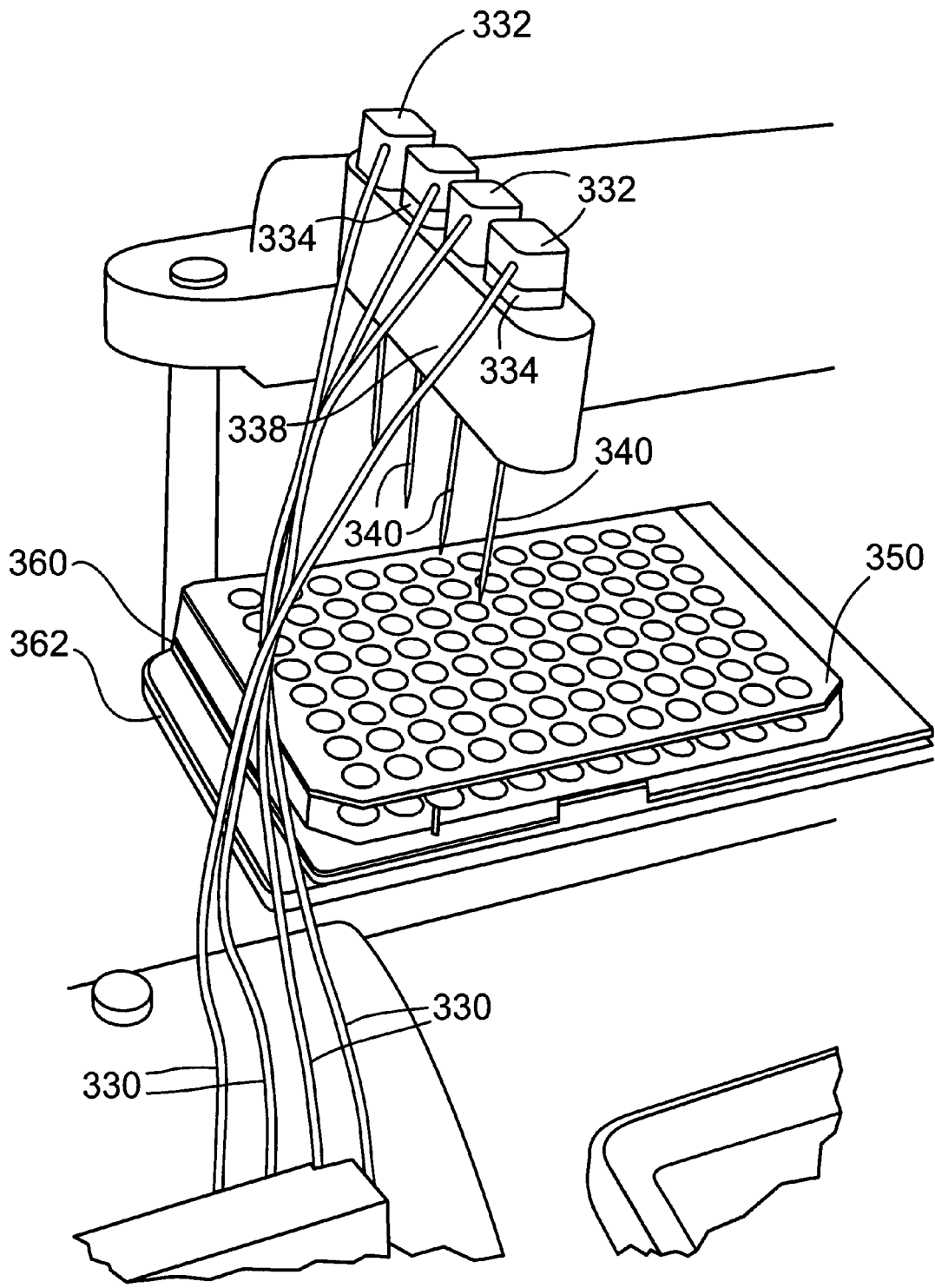
FIG. 3B shows a close up view of a portion of the two-axis fluid handling robot and a portion of the fluid control module.

FIG. 3B shows the sample containers 350 loaded onto an aluminum sample rack 360 which makes contact with a temperature control plate 362. The temperature control plate 362 maintains the aluminum sample rack 360, thereby sample container 350, and thus the fluids held within the sample container 350 at the user defined temperature setpoint. The temperature of the temperature control plate 362 may be controlled by means of resistive heating, thermoelectric elements, or circulating temperature control fluids. Exemplary temperature control characteristics of the temperature control plate 362 are:
Range: 4-40 deg C.
Precision: +/−1 deg C.
Accuracy +/−2 deg C.

In addition to the sample container 350 on the two axis fluid handling robot 20 (FIG. 1) there is a drip-well 364 (FIG. 2) which captures fluids which may escape from the probes 340 when the injection molded fittings 332 are removed from the quick connect fittings 334. Referring to FIG. 3A a wash/waste station 344 is provided with a construction that may include a 125 mL Nalgene bottle with a custom injection molded cap. The functionality of the wash/waste station 344 is to provide; a wash-station 370, including four wash wells 376 which receive wash solution from probes 340 after the probes have been aligned with their associated wash wells 376. The four wash wells 376 are individually separable from the others, allowing for individual configurations such that the washing characteristics may be matched to different configurations of the probes 340.

The inside walls and outside walls of each of the probes 340 can be washed using wash buffers that are delivered through the probes 340. A trough 372 allows for waste fluids exiting the probes 340 to be directed toward the waste bottle (not shown) situated directly beneath the waste/wash station 344, and attached to the waste/wash station. Optionally a port 380 allows wasted buffer flowing through tube 342, from the pumps 300 and 302, and valve 308 without passing through the sensors 316 or probes 340 to be collected in the waste bottle (not shown).

The configuration of the waste/wash station 344 and the sample container 350 is such that they may be readily removed and replaced manually or using simple laboratory robotic systems.

The two-axis fluid handling robot 20, the temperature controlled sample container 350, a drip-well 364 (FIG. 2), and the waste/wash station 344 (FIGS. 2 and 3A) is a separate sub assembly that can easily be separated from the rest of the instrument. This modularity is very advantageous to allow removal and disposal in the event of biohazardous contamination.

The present apparatus may use several different sample containers, including 96 well micro-titre plates and 48 well micro-titre plates both compliant with SBS standards, 1.8 mL BD Freezer vials, 1.0 mL Eppendorf tube and 0.5 mL Eppendorf tube.

The fluids can flow through the fluid control module 16 in user configured specified routes or combinations thereof, of which the following are four non-limiting examples:

1) From the bulk reagent bottles 306, 309, and 311, through the tubing 307 multi-port valve 308 and/or pumps 300 and 302, and through the waste line 342 directly to the wash/waste station 344.
2) From the bulk reagent bottles 306, 309, and 311, through the multi-port valve 308 and/or pumps 300 and 302, through one or more of the four sensors 316, through one of the four probes 340, and into the waste station 372.
3) From the bulk reagent bottles 306, 309 and 311, through the six-way valve 308 and/or pumps 300 and 302, through one or more of the four sensors 316, through one or more of the four probes 340, and into the wash station 370.
4) Samples or small volume reagents can be aspirated (pumped) back to the sensors 316 through tubes 330 from the sample containers 350, and delivered to, and incubated in, one or of the sensors 316, and subsequently dispensed from one or more of the four probes 340 into the waste station 372.

It will be clear to those skilled in the art that alternate fluid handling sequences can be supported using the existing hardware, for example, dilutions, combinations, mixing, reclamation of effluent samples/reagents, and the like.

While the fluid control module 16 has been described with various components these are only exemplary and may be substituted with other components. For example syringe pumps 300 and 302 may be replaced with peristaltic pumps, other types of piston or rotary pumps, electro-osmotics devices, pressurized fluid delivery means, and/or multi-channel pipetting systems. The functions of the various valves, connectors, and manifolds in the instrument 10 can be replicated using networks of two-way valves, integrated manifold based systems, micro-fluidic systems, and combinations thereof.

Sample and reagent introduction is accomplished by the user loading samples and any required reagents into a SBS 96 well microtiter plates and/or bulk buffer containers and executing a prepared assay protocol which delivers fluids at desired volumes, times and flow rates to the disposable sensor 316. Protocols may be user determined within the constraints of system hardware.

The control software may be configured so that assays may be run in the four sensors 316 sequentially (one protocol completes before initiation of another) or interleaved (the protocol for each sensor 316 is started when system hardware is available).

Data is represented graphically on screen 14 as it is generated as detector output plotted on a time scale. The user can determine the details of presentation choosing for example to show data from all analyte-receptor patterns 412 on all sensors 316 or selecting specific assay locations for onscreen presentation. Data files are generated corresponding to each sensor position and are exportable in standard formats for off line analysis in standard programs (MS Excel™, GraphPad Prism™, or in customized data analysis programs).

Sensors

The sensors 316 each include a molded plastic housing and are preferably constructed as a consumable with one or more preselected patterns on a planar surface of the consumable as disclosed in United States Patent Publication No. US-2005-01480635-A1 with a publication date of Jul. 7, 2005 entitled: DISPOSABLE REACTION VESSEL WITH INTEGRATED OPTICAL ELEMENTS, which is incorporated herein in its entirety by reference.

FIG. 4 shows an assembled view of the disposable sensor 316 with the liquid tubes 320 and 330, and the fluidic fittings 318 and 332, respectively, coupled thereto and an upper lid 402 designed to mate with patterned prism 400. More specifically FIG. 5 shows an exploded view of a portion of disposable sensor 316 wherein it is illustrated that upper lid 402 mates with patterned 400 which when assembled forms a defined interior chamber to allow flow of fluids across the analyte-receptor patterns 412.

Figure 6:
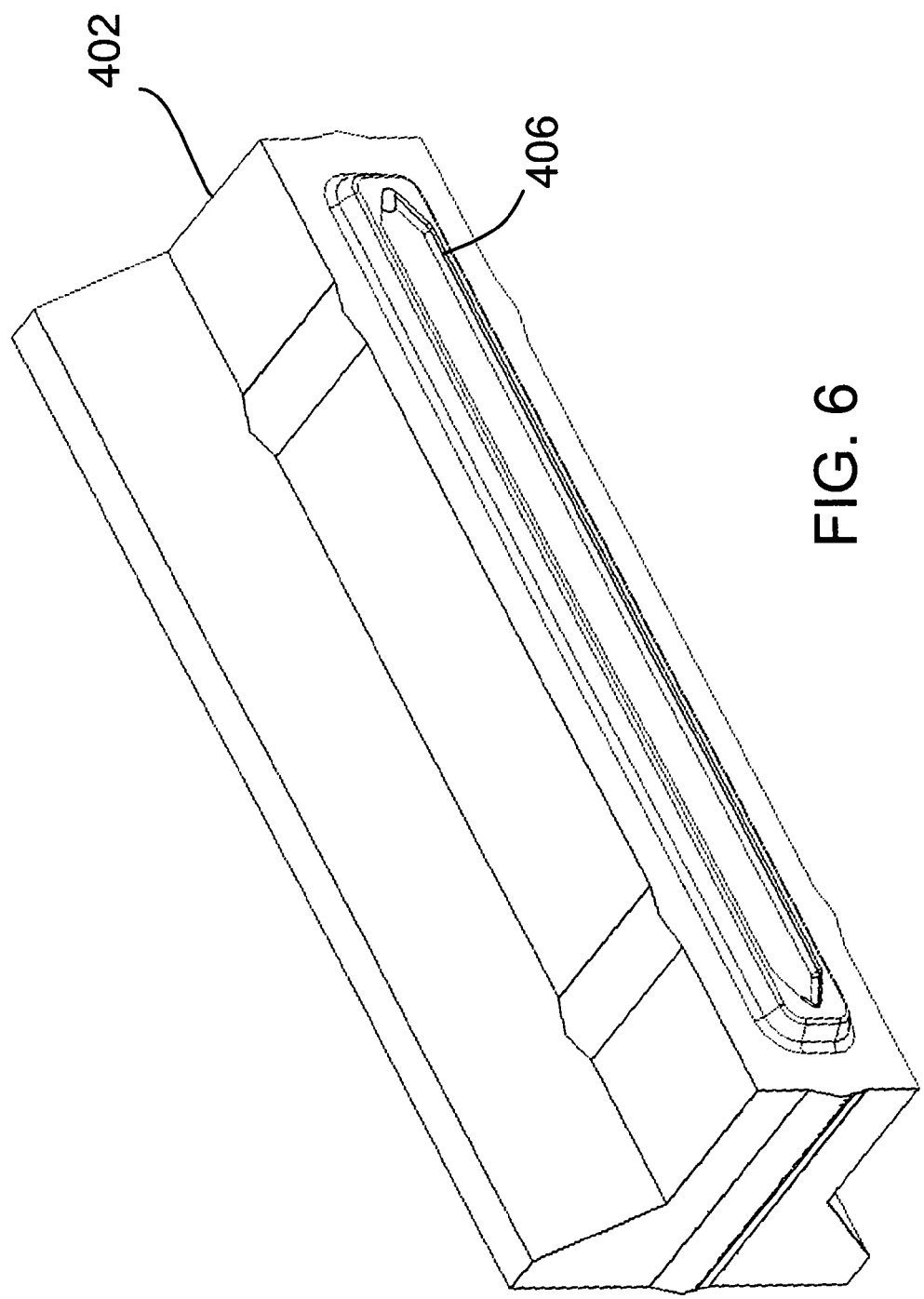
FIG. 6 shows an enlarged view of a part of the disposable sensor shown in FIG. 4.

Upper lid 402 includes a lip 406 which in this embodiment helps define the chamber and provides alignment features for assembling lid 402 with patterned prism 400. FIG. 6 shows a slightly enlarged view of the bottom of upper lid 402 The tubes 320 and 330 provide connection to the lid 402 to provide the fluid connection to the chamber in sensor 316. This described structure allows connection to fluid control module 16 described in detail previously. Patterned prism 400 as shown in this exemplary embodiment includes an integrally formed optical element 410 through which light accesses the analyte-receptor patterns 412 (FIG. 1A) within sensor 316 from the optical subsystem described hereinafter and from which emerges the diffracted light beams which then enters the detector in the optical subsystem.

Referring to the schematic drawing of the interior of the optical element 410 as shown in FIG. 1A it can be seen that the inner surface of optical element 410 has one or more analyte-receptor patterns 412 formed thereon, which may be identical for redundancy or they may be different patterns and/or different receptors.

In an embodiment of the sensors 316, the bottom surface of optical elements 410 have four (4) pre-selected analyte-specific receptors patterns spaced from each other but there may be more or less patterns as described with respect to FIG. 1A above. Details of one non-limiting and exemplary method of depositing these preselected patterns on a substrate is disclosed in U.S. Pat. No. 6,981,445 issued to Cracauer et al. on Jan. 3, 2006 entitled: Method And Apparatus For Micro-Contact Printing, which is incorporated herein in its entirety by reference.

Figure 13A:
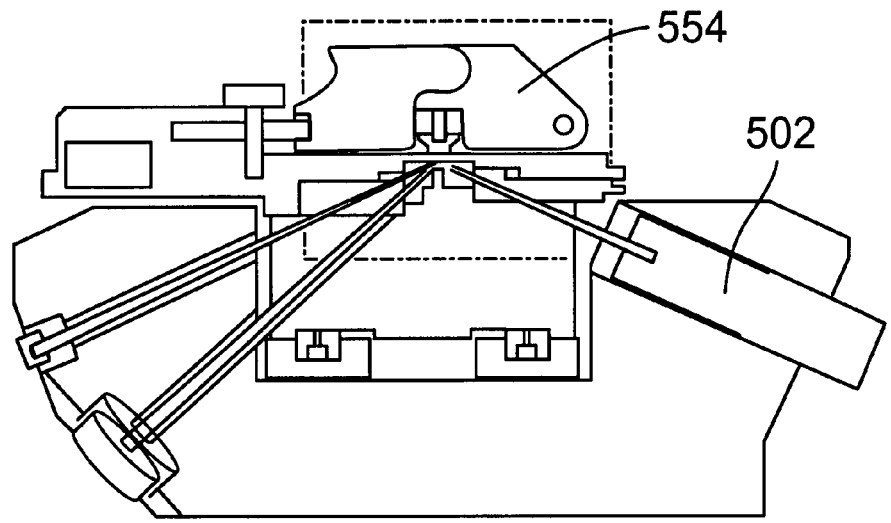
FIGS. 13A and 13B show schematic cross sectional views of the optical subsystem illustrating the workings of the system interlocks.

Prior to operation, the sensors 316 are inserted into the sensor station 19 stations in the optical subsystem 460 and a clamp 554 shown in FIG. 13 is closed which includes an interlock system to ensure the laser beam is not turned on until the interlock system is engaged.

Optical Subsystem

Figure 8:
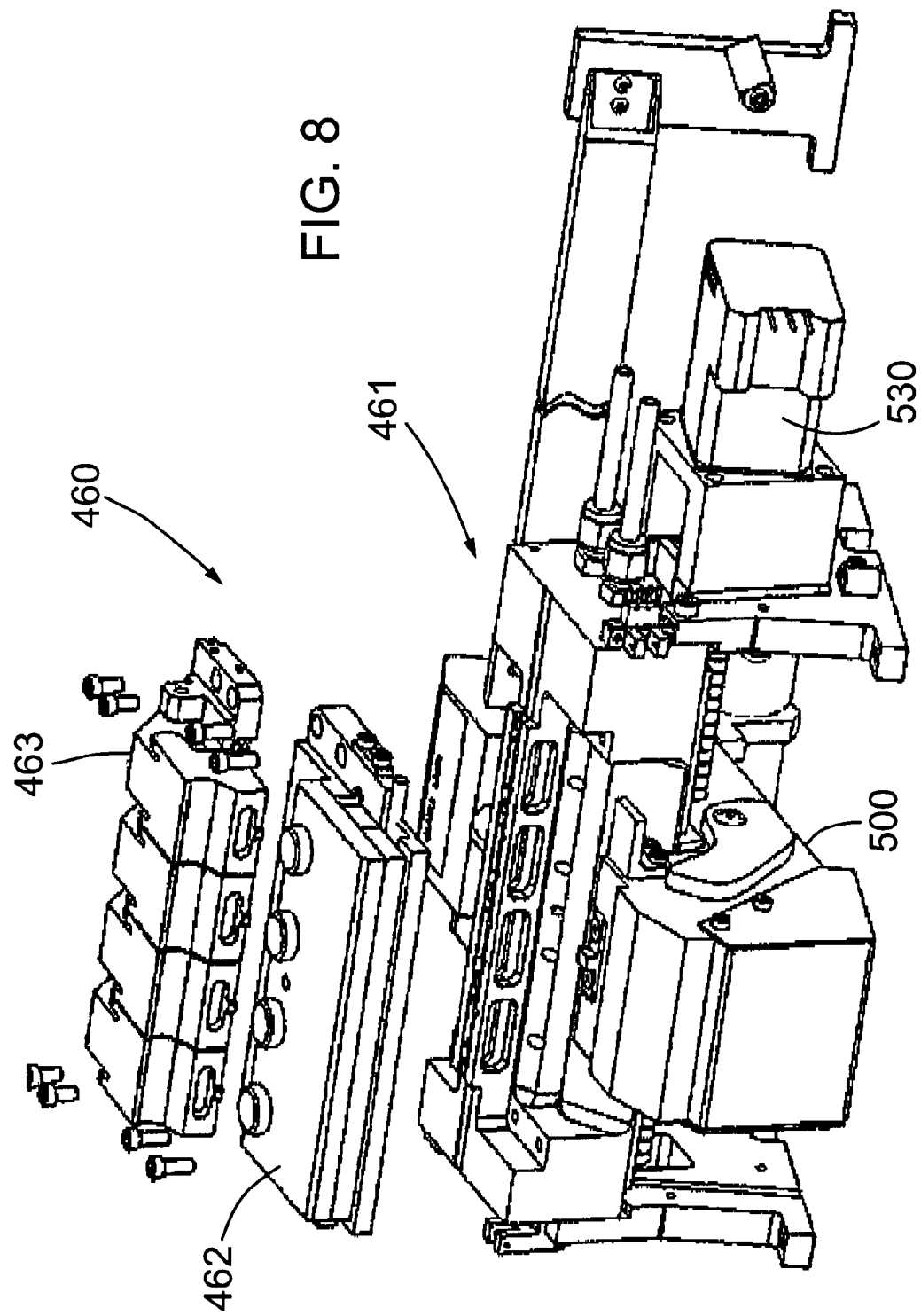
FIG. 8 shows an exploded view of the optics subsystem shown in FIG. 7.
Figure 9:
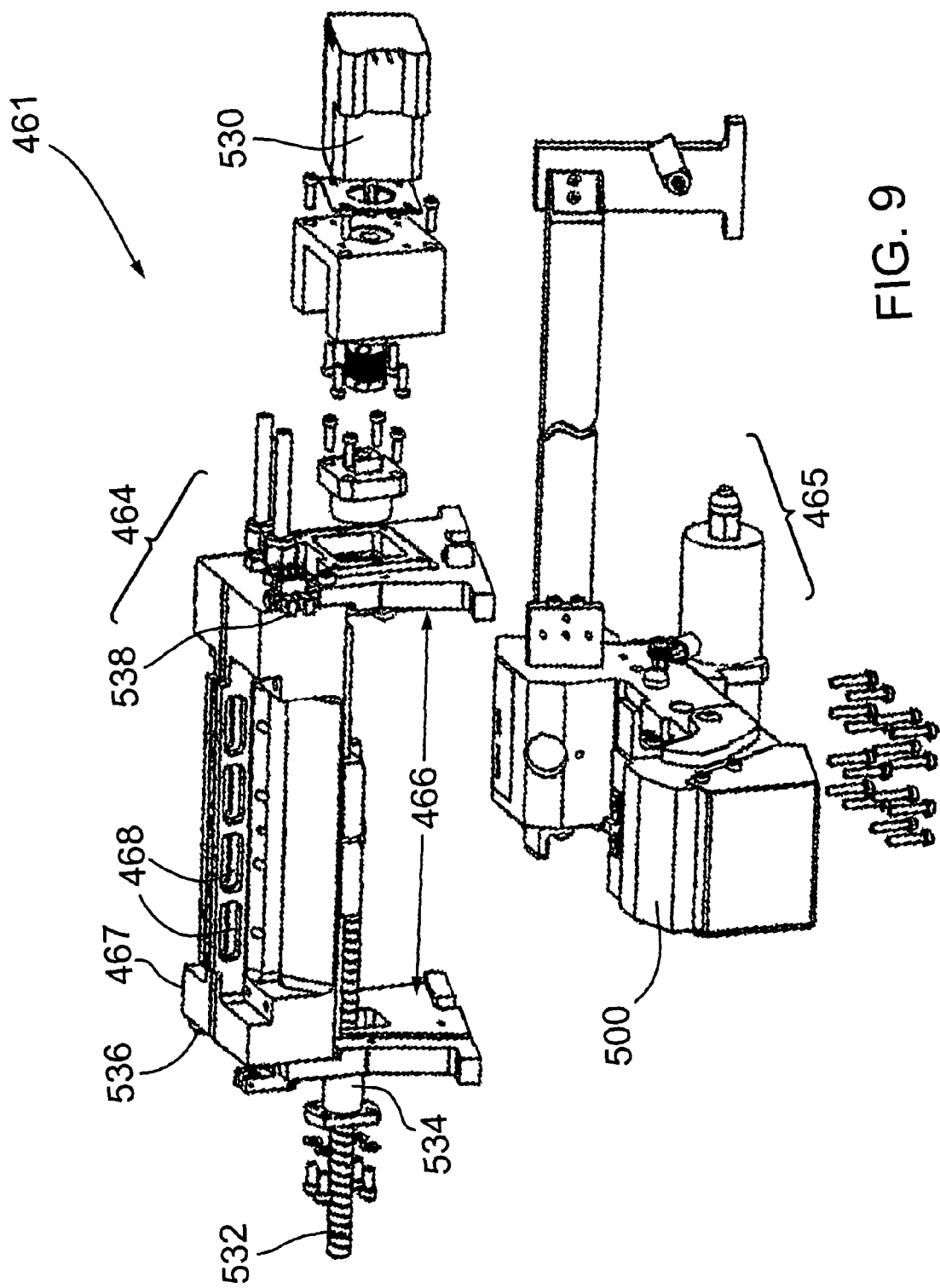
FIG. 9 shows an exploded view of the main structure assembly forming part of the optical subsystem shown in FIG. 7.

As seen in FIG. 8, the optical subsystem 460 (FIG. 7) is comprised of the main structure assembly 461, the latch side assembly 462, and the clamp side assembly 463. FIG. 9 shows an exploded view of the main structure assembly 461 which is comprised of the frame assembly 464 and the block assembly 465. The frame assembly 464 is comprised of two supports 466, one connected to each end of prism bed 467. The prism bed 467, made of machined and anodized aluminum, is the main component in the optical subsystem 460 responsible for positioning the sensor 316 (not shown) in the optical path. The prism bed 467 contains four sensor receiving structures 468 (but could be configured to include more or less), each capable of accepting one sensor 316.

Figure 10:
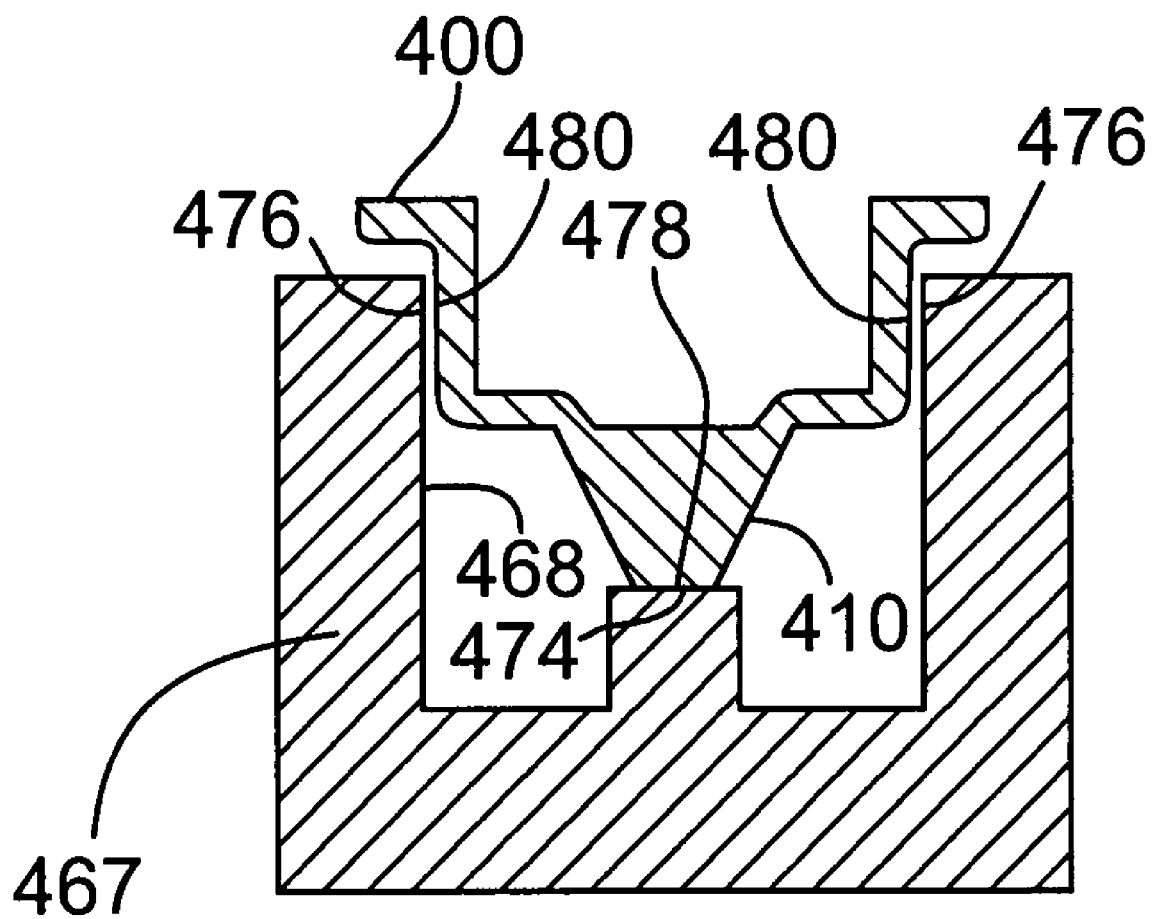
FIG. 10 shows a schematic cross sectional view of a sensor receiving structure with a part of the sensor in place.
Figure 11A:
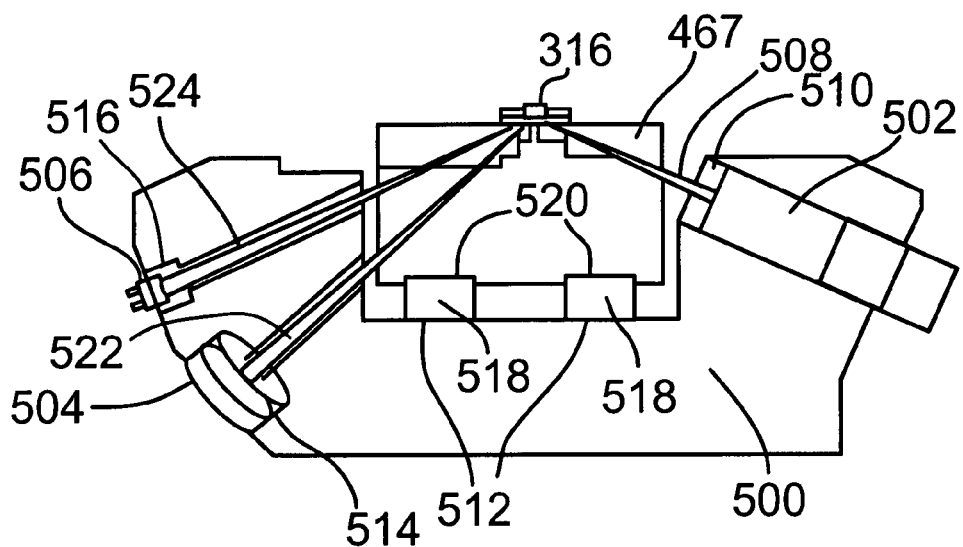
FIGS. 11A, 11B, 11C and 11D show multiple schematic views of the optical path implemented in the analyzer by the components of the optical subsystem shown in FIG. 7 and a disposable sensor shown in FIG. 4.
Figure 11B:
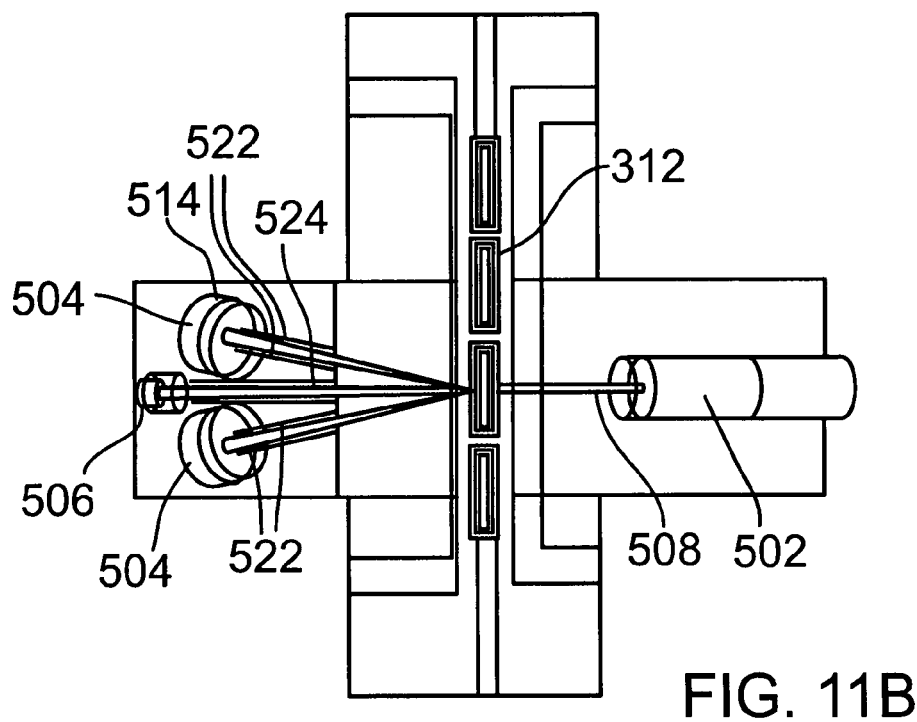
Figure 11C:
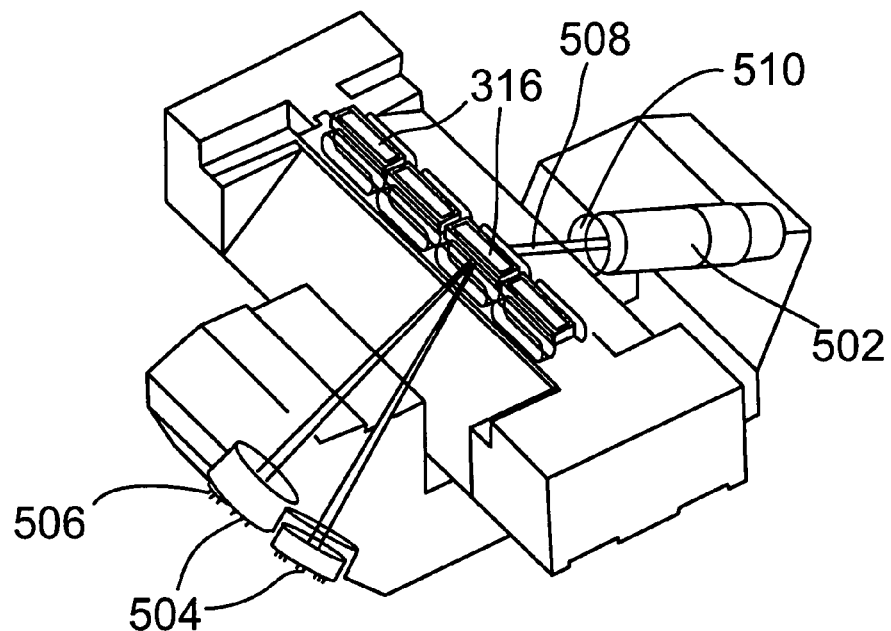
Figure 11D:
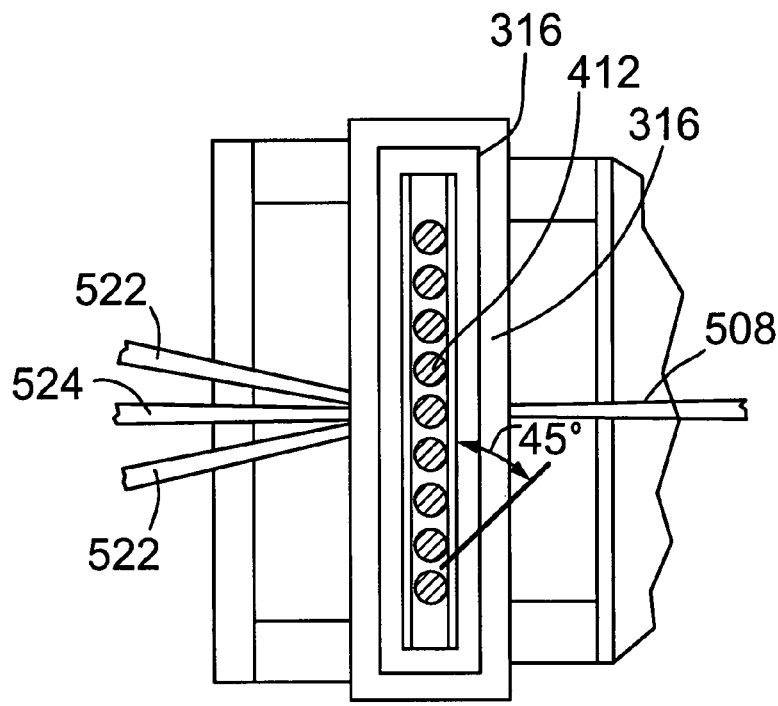
Figure 12:
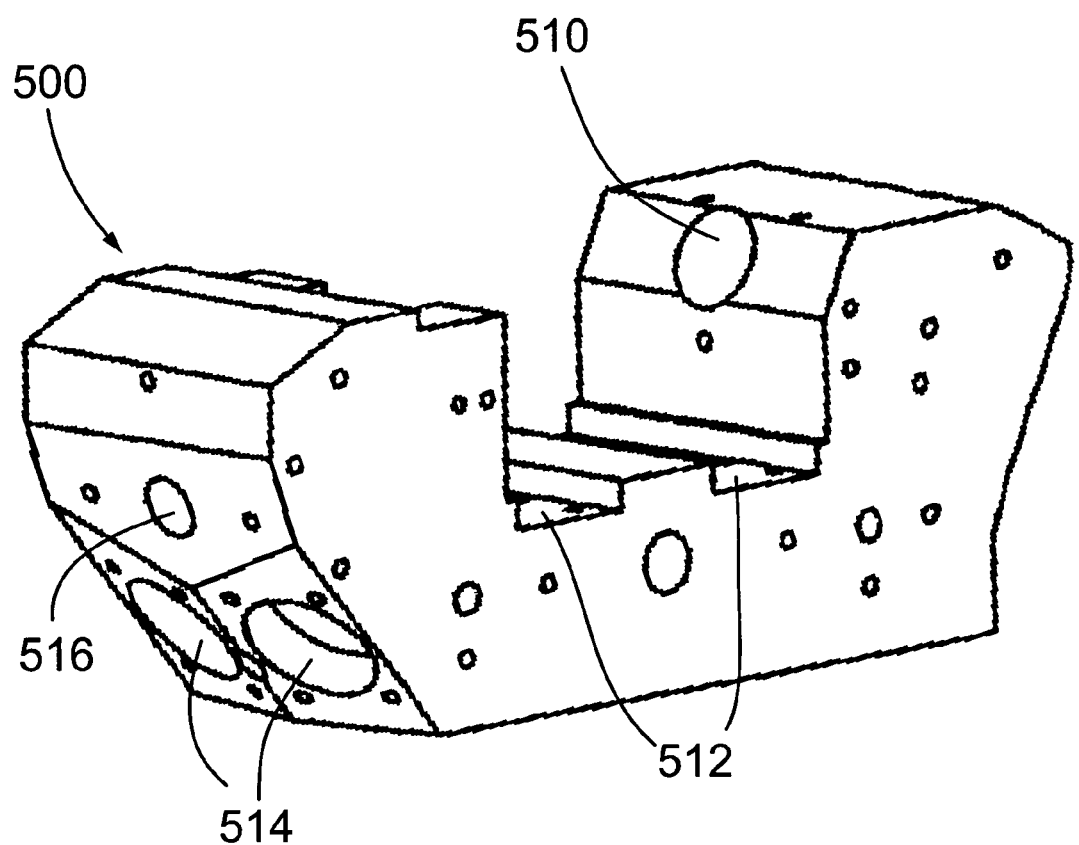
FIG. 12 shows multiple views of the optical block which a component of the optical subsystem shown in FIG. 7.

The sensor receiving structures 468, essentially identical to one another, match the form fit of the patterned prism 400 and provides contact surfaces 474 and 476 shown in FIG. 10 which is a cross-sectional schematic showing the relationship between the patterned prism 400 and the sensor receiving structures 468 contained within the prism bed 467. Feature 474 is an essentially planar element of the sensor receiving structures 468 to which feature 478, an essentially planar element of the optical element 410 registers. This registration establishes one axis of optical alignment between the optical element 410 of the patterned prism 400 and the prism bed 467. Additionally this registration is the primary location of heat transfer between the prism bed 467 and the sensors 316. Features 476 are essentially planar elements of the sensor receiving structures 468 to which features 480, an essentially planar element of the patterned prism 400, register. This registration establishes lateral alignment of the optical element 410 to the prism bed 467. Additionally this registration is a secondary location of heat transfer between the prism bed 467 and the sensors 316.

This configuration advantageously provides precise positional locationing of the optical element 410 relative to prism bed 467 at a location in closest proximity to the relevant optical surfaces of optical element 410. This registration therefore provides the necessary optical alignment between the sensor 316 and the prism bed 467 while at the same time providing the necessary thermal control at a location close to the patterns and fluid channel in the sensor 316. Since both thermal drift and optical misalignment may cause a rapid degradation of signal integrity this configuration is highly advantageous.

The prism bed 467, thereby the sensor(s) 316, as they are in thermal contact, may be temperature controlled in the range from about 4 to about 40 deg Celsius as an example.

Referring to FIG. 11A through FIG. 11D the optics block 500 is the structural component, made of machined and anodized aluminum, which holds the laser-head 502, at least one diffraction signal detector 504, and optionally a reflected main beam detector 506 in a fixed reference relative to each other. The laser-head 502 houses a red laser diode (not shown) whose emission is a laser beam 508 co-linear with the centroid of the outer shell of laser-head 502, thus allowing for the alignment of the laser beam 508 with respect to the optics block 500 to be determined by the mechanical precision of the machined bore 510 relative to optical block mounting bores 514 and 516, where the two bores 514 receive the signal detectors 504, and bore 516 receives the reflected main detector 506. Additionally, the precision of the fit between the laser head 508 and the bore 510 facilitates the establishment of a stable thermal relationship between the laser head 508 and the optics block 500. The unitary structure of the block 500 facilitates highly precise machined relationships without secondary assembly tolerances affecting the precision of the optical alignment. Additionally, this unitary construction minimizes the affects of thermal expansion and contraction on the optical alignment of all optical elements within the block assembly 465. It will be understood that the laser head may house a variety of laser diodes of appropriate wavelength and power and may house additional optical conditioning elements to shape and direct the beam.

Two linear rails 518 link the prism bed rail reference surface 520 to the block rail reference surfaces 512 thereby establishing a reference between the block assembly 465 and the sensors 316. These two linear rails 518 provide the mechanical reference between the block assembly 465 and the frame assembly 464 and allow longitudinal motion with respect to sensor 316 enabling presentation of each analyte-receptor patterns 412 on each sensor 316 to the laser beam 508 and transmission of the diffraction beams 522 and the reflected main beam 524 to diffraction signal detectors 504 and reflected beam detector 506, respectively. Linear rails 518 must be of adequate precision to satisfy the required optical alignment tolerances. Components of the required precision (15 to 25 micron true position) are readily commercially available at reasonable cost. However, the disclosed embodiment describing the linear rails 518 as the linkage between the block assembly 465 and the frame assembly 461 are merely exemplary, and it should be understood that this linkage may be embodied as a vee-groove and vee-feature linkage, a dovetail slot and dovetail feature linkage, integral bearing configurations, and the like.

In this embodiment at least one diffraction beam 522, and optionally at least one additional diffraction beam 522, and optionally a reflected beam 524 are monitored by pre-amplified photodiode optical detectors 504 and 506 respectively. The detectors 504 and 506 are constructed using industry standard outer housing dimensions. The precision of the relative position of the detection surface to the housing, and the precision of the housing dimensions are such that detectors 504 and 506 may be placed into bores 514 and 516 without the need for alignment or adjustment thus increasing reliability and reducing cost. This configuration also thermally couples the detectors 504 and 506 to the optics block 500. In order to stabilize the electronics and to minimize the affects of thermal gradients induced by changes in the ambient temperature of the operating environment, the temperature of the optics block 500 is controlled to a fixed temperature above ambient. Various other types of optical detectors may be used, for example, CCDs, PMTs, and the like. The microprocessor controller is configured to compare the diffracted light signals captured by optical detector 504 and the reflected light signals captured by the second optical detector 505 for purposes of calibration.

Referring again to FIG. 9 a stepper motor 530 generates the force required for the longitudinal motion of the block assembly 465 by rotating ball screw 532 to which it is coupled and which is essentially axially static relative to the frame assembly 464. The nut 534 is mounted to the block assembly 465 and translates the rotational motion of the ball screw 532 into linear motion of the block assembly 465 in the longitudinal direction with respect to the prism bed 467. A home switch 536 and a limit switch 538 provide a positional reference and travel limit, respectively, for the block assembly 465 that feedback to the logic control system under the control of the microprocessor. Thus, in this embodiment the structure containing the detectors 504 and 506 and the laser head 502 moves with respect to a static structure holding the sensors 316. This is the preferred embodiment as it enables the tubing 320 and 330 (FIG. 4) leading to the sensors 316 to remain essentially stationary. This is beneficial as it avoids undesired movement of fluids within the sensors 316 which may be present in an alternative configuration whereby the structure holding the sensors 316 moves with respect to a static structure containing the detectors 504 and 506 and the laser head 502. This fluid movement may result from inertial forces as the sensors 316 and the fluids therein experience forces due to acceleration and volumetric changes in the tubing 320 and 330 as it flexes. Notwithstanding these possible drawbacks, this alternative configuration could also be employed.

The overall structure of the optical subsystem 460 facilitates a precise and robust alignment of optical elements while allowing for a single source (laser) and a single detector to address multiple analyte-receptor patterns 412. The use of a single source and detector reduces the need for compensating for variability inherent with multiple sources and detectors, in a cost effective manner. Alternative means could be used to accomplish this single source and detector relationship. Examples are beam splitters, fiber optic conduits, micromirror arrays and the like. These solutions bear additional complications in either required alignments at assembly, additional high precisions components, additional high tolerance machining steps and increased sensitivity to induced temporary or permanent misalignment of the optical path resulting from impact or vibration. Notwithstanding these drawbacks, the aforementioned embodiments may be employed.

Referring to FIG. 8 the clamp side assembly 463 and the latch side assembly 462 are mounted to the main structure assembly 461, and apply a force to the upper surface 319 of the upper lid 402 which transfers to the patterned prism 400 ensuring that it is properly seated in the sensor receiving structures 468, and provide means to prevent the operator from gaining exposure to laser radiation levels beyond acceptable limits by means of a mechanical interlock.

Figure 13B:
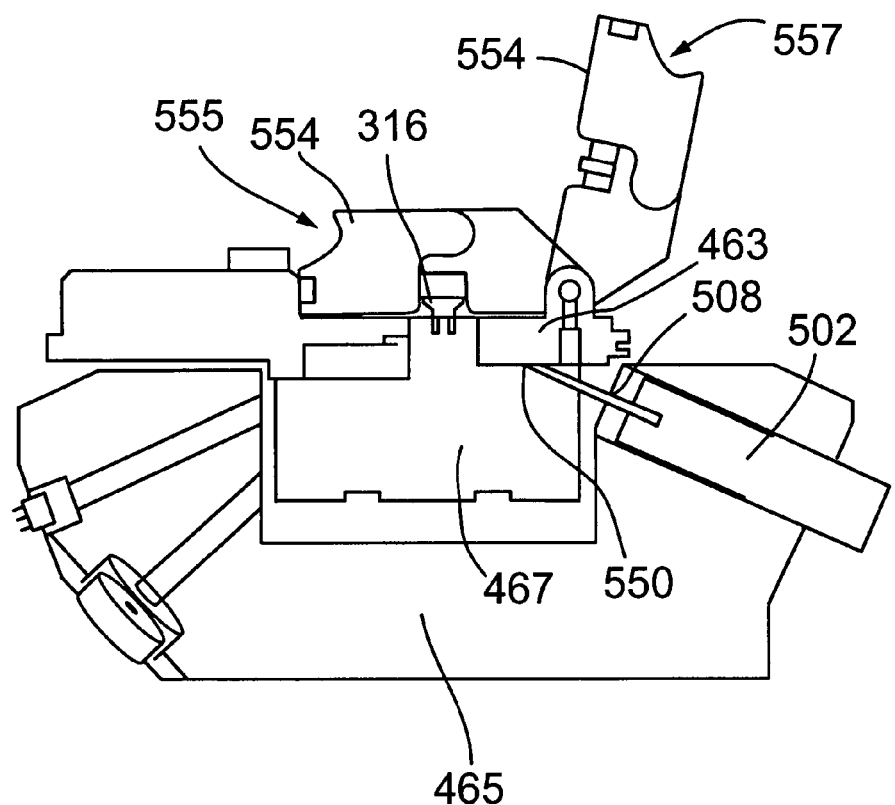

Referring to FIG. 13B, there is a position at one extent of the travel of the block assembly 465 where the laser beam 508 is blocked by a feature 550 on the clamp side assembly 463 before it can encounter the sensors 316, and this position is referred to as the safe position FIG. 13B. While the block assembly 465 is in the safe position as shown in FIG. 13B the clamps 554 can be freely opened 557 and closed 555.

Figure 14A:
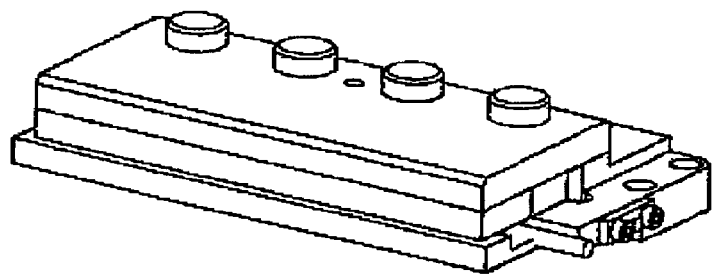
FIG. 14 shows a) an assembled view of the latch side assembly which positions and/or seals the disposable sensors in the analyzer and b) an exploded view thereof.
Figure 14B:
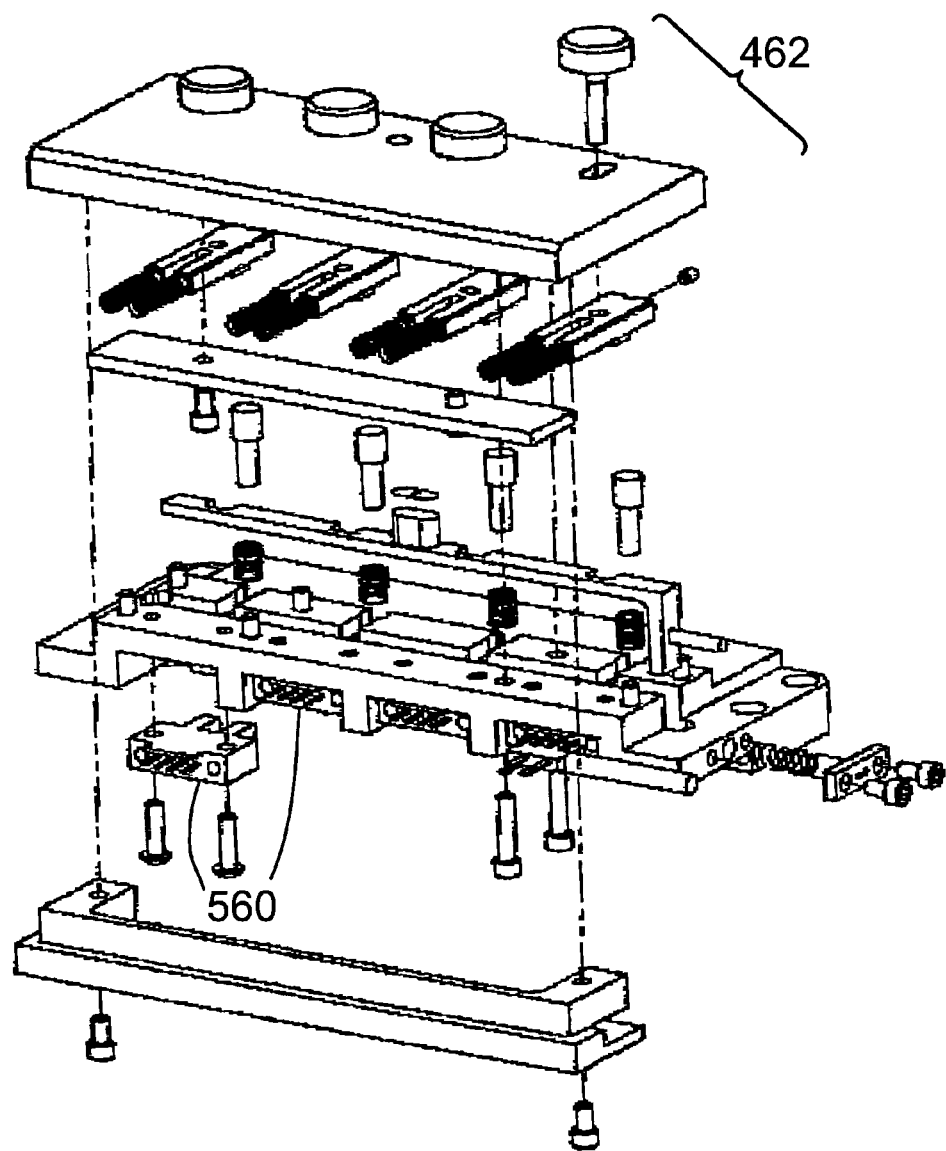
Figure 15:
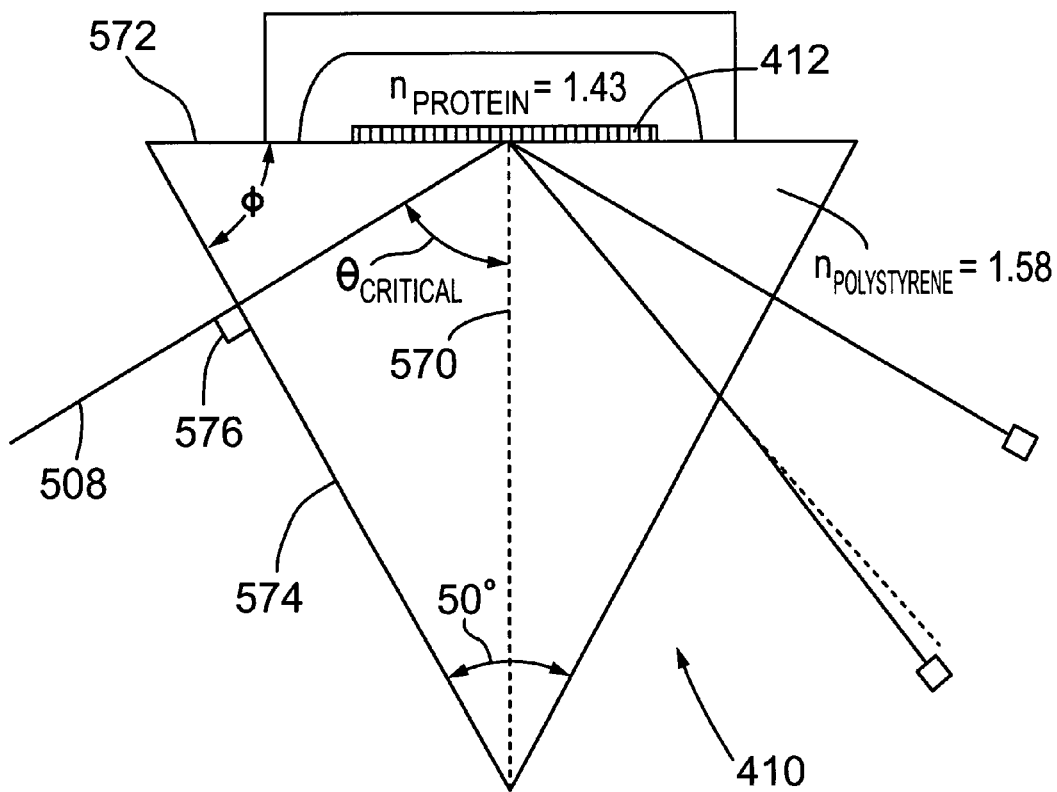
FIG. 15 show a schematic cross sectional view of an exemplary optical element and relevant angles and optical paths for obtaining total internal reflection given the particular materials being used for the optical element and analyte-receptors patterns.

FIG. 14 A shows the assembled latch side assembly 462 and additionally, as seen in the FIG. 14B, an exploded view of the latch side assembly 462, optical sensors 560 within the latch side assembly 462 monitor if the clamps 554 are in the closed 555 position. The logic control system under the microprocessor computer control will not instruct the stepper motor 530 to move the block assembly 465 out of the safe position FIG. 13B unless all of the clamps 554 are closed 555 position. Furthermore, once the clamps 554 are all closed 555 position, and the stepper motor 530 has moved the block assembly 465 out of the safe position FIG. 13B a mechanical interlock prevents the operator from moving the clamps 554 to the open 557 position. Should the clamps 554 become opened 557 while the block assembly 465 is not in the safe position FIG. 13A, power to the laser head 502 is cut, thereby turning off the laser beam 508. Once the block assembly 465 returns to the safe position FIG. 13B power to the laser head 502 is restored, thereby restoring Referring to FIG. 15 a schematic view of the optical element 410 of the patterned prism 400 shown in transverse cross-section, in order to ensure that the instrument 10 operates in total-internal-reflection given the material of which the optical element 410 and the analyte-receptor pattern 412 are composed, the angle made between the incident laser beam 508 and the vector 570 normal to the patterned surface 572 of the optical element 410 which is referred to as the critical angle is a function of the indices of refraction of the material of which the optical element 410 is comprised and the material used to generate the analyte receptor pattern 412 on the patterned surface 572. In this embodiment the critical angle is 65 degrees thus the angle between the incident laser beam 508 and the patterned surface 572 is 25 degrees. Thus to maximize coupling of the incident laser-beam 508 power into the analyte-receptor pattern 412, the optical element 410 is comprised of a triangular prism such that the incident optical surface 574 forms a right angle 576 with the incident laser-beam 508. Thus the angle between the optical surface 572 and the incident face 574 must equal 25 degrees.

It has been determined that the performance of the instrument 10 is optimal when the lines of the analyte-receptor pattern 412 are rotated at an angle of 45 deg relative to the longitudinal axis of the sensor 316. In this orientation the signal-to-noise ratio is maximized. While this angle is advantageous other angles may be used effectively.

Alternative means of precisely identifying the location of the analyte-receptor pattern array 411 (FIG. 1) on each patterned prism 400 have been implemented. These means are dependent on the interrogation of the sensor 316 by the laser beam 508, the precision and repeatability of the array 411, and precision and repeatability of the stepper motor 530 and lead screw 532 and nut 534. Scanning longitudinally across the array 411 produces a distinctive pattern of high and low signal intensity when signal is plotted against position. The signal values may be analyzed and compared to the theoretical pattern generated by a sensor scan. The scanned pattern is then matched in software to the theoretical pattern and locational references in the system software are adjusted accordingly. This adjustment produces an essentially exact map of the analyte-receptor pattern 412 locations relative to the optical subsystem 460 without the need for a home sensor or other means of mechanical alignment. Since this alignment references the analyte-receptor patterns 412 and the optical path directly, no intervening variabilities in optical subsystem 460 construction which impact the axis of scan are relevant, nor are any variabilities in sensor fabrication resulting in minor alignment errors of the array 411 to the patterned prism 400 relevant. The matching of the expected signal pattern to the actual pattern measured by the instrument 10 is accomplished by a simple lowest-quartile-filter, thus establishing the location of the expected regions of low signal between the analyte-receptor patterns 412. This pattern is then cross correlated to the expected pattern and the locational references in the appropriate software files are adjusted for the individual sensors 316. Other means of detecting the analyte-receptor patterns 412 and subsequent correlation to the file locations are possible. For example Fourier transform techniques could be employed to match a portion of one entire scan or a portion thereof to the expected scan. Examination of a single analyte-receptor pattern 412 or any number of analyte-receptor patterns 412 either in whole or part could provide adequate information to allow registration of the array 411 to the optical subsystem 460.

A means has been implemented in the system software to allow selection of preferential regions within each analyte-receptor pattern 412. A variety of deviations in the analyte-receptor pattern 412 may cause signal elevations or depression in localized regions of a given analyte-receptor pattern 412. Examples are: light scatter caused by small defects and scratches in prism 400 fabrication or during initial pattern deposition, particle contamination on any of the optical surfaces, areas of incomplete deposition of the initial analyte-receptor pattern 412, inhomogeneities or inclusions within the bulk of the molded prism 400. With careful processing methods, these defects are most often confined to small regions and may be systemic in nature; for example defects in the prism 400 caused by defects in the injection mold surfaces. These defects may be random in nature caused by particulate contamination and the like. In the former case, the defects could be minimized by resurfacing the tooling faces causing the defect, but this presents a costly and iterative process as new defects may arise in the normal course of processing. Also, in some cases these defects may be reflective of inclusions or grain boundaries in the metal the tool is constructed from. In the latter case, even careful controls will not eliminate all defects and in any event cannot address contamination occurring immediately prior to use. In this embodiment a scan of each sensor is conducted prior to initiation of a binding reaction. This scan gives a baseline signal intensity reading of the sensor 316 analyte-receptor pattern(s) 412. It should be noted that this baseline scan can be replaced by or supplemented with scans taken after binding reactions have occurred. These scans have value described hereinafter.

A perfect sensor 316, when scanned by the instrument 10 would in principle produce a signal output that would, when plotted against location along the axis of the scan, resemble a square wave with the peaks representing those locations where the laser beam 502 is interrogating an analyte-receptor pattern 412 and the troughs indicating areas on the patterned prism 400 that are unpatterned. The transitions between peaks and troughs are not step changes, but are rather sloped, reflecting the entry of the laser beam 502 onto the analyte-receptor pattern 412. Once the entire beam 502 is contained within the area proscribed by the analyte-receptor pattern 412, the theoretical signal is constant until the laser beam 502 begins to leave the analyte-receptor pattern 412 area.

In practice, the peak signal level is not flat or of stable value. The aforementioned defects produce areas of high or low signal values depending on the nature of the defect. These deviations in and of themselves do not in many cases eliminate the utility of any particular region of the analyte-receptor pattern 412. Often, binding reactions still occur and the change in signal intensity is still proportional to the degree or amount of binding to surface receptors. In a limited number of cases however, productive use of a particular area is compromised by areas of signal deviation. Examples are regions where the defect causes so much scatter so as to exceed the dynamic range of the detection system. In this circumstance, subsequent binding events cannot be detected Another example is a situation where a rapid transition from a normal signal to a very high or very low signal occurs. In this case, extremely small movements (on the order of 25 microns) of the beam relative to the analyte-receptor pattern 412 can either inject noise into the signal due to vibration and the like, or in the case where multiple analyte-receptor pattern 412 are being monitored concurrently, produce offsets in the data stream due to small inaccuracies in the return of the block assembly 465 to the previously interrogated location.

In practice, it has been determined that interrogating regions of the laser beam 508/analyte-receptor pattern 412 interface with a scan resolution of about 25 microns is sufficient to reveal significantly degraded interrogation regions. A number of methods to evaluate the severity of the degradation are possible. In this embodiment, a comparison of signal level on adjacent regions within analyte-receptor patterns 412 is made using system software. Consecutive comparisons of adjacent regions are made until a best group or adjacent regions may be selected. Groups may range from two to eleven regions. Three to five regions are normally sufficient. The region at the geometric center of the group is then selected as the region where all subsequent interrogations of each analyte-receptor pattern 412 is performed. Selection criteria include but are not limited to signal range withing the selected region, amplitude difference relative to the local or distributed trough signal level, amplitude difference relative to mean analyte-receptor pattern 412 or sensor 316 values at peak location, amplitude relative to detector dynamic range, and combinations of the parameters.

A number of techniques to select preferred interrogation regions are available and may be tailored to specific analytical requirements. For example a rudimentary case can prioritize by demanding a specific maximum deviation from mean value within a given group of regions, coupled with a secondary requirement that the absolute signal be between two specified values. This would be useful in almost all analytical cases to avoid regions of rapid signal slew, regions of high signal (indicative of high scatter) or a zone of incomplete pattern resulting in low signal. More sophisticated selection analysis might include setting bounds per the above example, but adding a restriction to closely match values for one analyte-receptor pattern 412 relative to one or more analyte-receptor patterns 412 in the same sensor 316 or on other sensors 316 either currently in use or from previously determined values. This approach has value in improving inter and intra assay repeatability and precision. Yet more sophisticated criteria may facilitate selections of regions with surface capture molecules that are matched to other analyte-receptor patterns 412 or sensors 316, as the initial signal above the trough is indicative of total coverage. This analysis can be particularly useful when used with consecutive scans pre and post initial binding and/or dissociation events where the initial binding event is the deposition of a capture molecule and the binding event which is the subject of investigation occurs subsequent to the first binding event. Many other combinations of parameters and rankings are possible and the methods of the execution and benefits thereof will be obvious to one skilled in the appropriate art.

This embodiment of the system enables several means of attaching event markers related to transition points in the data set gathered during an experiment. Transition points of most relevance are events when a reagent, sample, or combination of reagents and/or samples arrive at the analyte-receptor pattern 412 or analyte-receptor patterns 412 being monitored. These transition events are of importance as they identify the precise moment a material is available to react with the analyte-receptor pattern 412. That is, they identify the precise starting point of the interaction. In any controlled system including the current invention, the approximate time of initiation of a reaction is relatively easy to control. However, most systems have inherent latencies between the time a command is issued to execute a movement of fluids, and the time that the commanded operation is completed. Latency, when consistent and well know is not intrinsically a problem. Variable latencies however, introduce a level of uncertainty in when an event actually occurs. Sources of variability include command execution time, uncertainties in response times of active components such as pumps and valves, lags in fluid delivery resulting form compression of air within fluid circuits, and communication delays between the main control device and active system components. In many cases small deviations in timing are insignificant.

In cases where very rapid reactions occur or when analytical methods such as curve fitting programs are used, results are enhanced by knowledge of the true starting time to the best degree possible. One technique available for attaching an event marker used with a diffractive optic systems is the fact that all else being equal, the signal generated is dependent on the refractive index of the medium in contact with the elements of the array 411 of analyte-receptor patterns 412. The current invention allows introduction of media of differing refractive index at any and all transition events. For example, an air bubble introduced between sequential reagents or samples will create a large spike in signal when it moves across the diffractive element because the index of refraction of air (approximately 1.0) is significantly different than the refractive index of the elements of the analyte-receptor pattern 412, and more significantly different than that of the reagents, buffers, samples or water typically used in experiments. The refractive index of these latter components typically ranges from 1.3 to 1.6 or thereabout. The presence of this large signal increase is readily identified and marked in the data stream by simple evaluation means in either standard or customized analysis programs such as MS Excel™ and GraphPad Prism™. The transition events can thus be temporally identified relative to the rest of the data stream essentially limited only by the granularity of data acquisition. Typically in the current invention, a data acquisition granularity of 100 milli-seconds is used. Therefore the temporal uncertainty of the arrival of a reagent can be determined within approximately 100 milli-seconds plus transition time across a portion of the beam. With proper selection of fluid flow rates, this second contribution to latency is minimal. At a relatively modest flow rate of 60 micro-liters per minute for example the transition time is below 100 milli-seconds. The uncertainty in this time is perhaps half the total.

It should be noted that even slight refractive index changes between fluids presented to the analyte-receptor pattern 412 are detectable. In this circumstance, a step change in the signal level can be noted as the transition point rather than a sharp spike depending on the specifics of the experimental reagents and samples used. Normal refractive index differences between reagents may be sufficient to produce a distinct, highly precise transition marker with temporal accuracy similar to that described above.

This embodiment enables either essentially continuous monitoring of a single analyte-receptor pattern 412 or serial iterative monitoring of multiple analyte-receptor patterns 412 depending on the needs of the experiment, thus enabling high resolution, real-time data collection or lower resolution intermittent data collection or combinations thereof.

The present invention has utility in many categories of experiments including but not limited to kinetic analysis of binding and/or dissociation reactions, endpoint analysis, sandwich and modified sandwich assays, amplified/enzyme substrate assays, examination of buffer conditions, reagent sample concentrations, matrix effects on reactions, comparisons of binding pairs for affinity, displacement assays, etc.

As used herein, the terms "comprises", "comprising", "including" and "includes" are to be construed as being inclusive and open ended, and not exclusive. Specifically, when used in this specification including claims, the terms "comprises", "comprising", "including" and "includes" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

Therefore what is claimed is:

1. An analyzer for performing chemical, biochemical or biological assays using diffraction of light, comprising;
    a disposable sensor including at least one sample well and at least one pre-selected pattern of analyte-specific receptors bound to a surface of said at least one sample well;
    at least one sensor station for receiving said disposable sensor;
    a fluid holding sample container for holding assay fluids used in performing said assays and samples being tested for presence or absence of analytes which bind to said analyte-specific receptors;
    a fluid flow and handling system in flow communication with said at least one sensor, sources of said samples and sources of said assay fluids used in performing said assays configured to deliver said samples and fluids to said at least one well in said disposable sensor and said fluid holding sample container, said fluid flow and handling system including fluid pump configured to pump fluids and samples from their respective sources to said disposable sensor, to said fluid holding sample container and to fluid waste containers, said fluid flow and handling system including a fluid dispenser configured to dispense samples and fluids to said fluid holding sample container and to dispense samples and assay fluids from said fluid holding sample container to said at least one sensor;
    a robotic manipulator connected to said fluid holding sample container configured to pre-position said fluid holding sample container with respect to said fluid dispenser;
    a temperature controller for controlling a temperature of an interior of the analyzer;
    an optical system for producing and directing a coherent beam of light toward said at least one sensor station to impinge on said surface of said at least one sample well containing said at least one pre-selected pattern of analyte-specific receptors bound thereto, said optical system including a first optical detector configured to measure diffracted light signals from said at least one pre-selected pattern of analyte-specific receptors;
    a scanning mechanism for scanning said coherent beam of light with respect to said at least one sample well containing said at least one pre-selected pattern of analyte-specific receptors bound thereto; and
    a microprocessor controller connected to said scanning mechanism, said scanning mechanism being configured to scan said coherent light beam across said surface in a controlled manner, and said microprocessor controller being programmed with instructions to scan said coherent light beam across pre-selected portions of said at least one pre-selected pattern of analyte-specific receptors prior to flowing sample containing the analytes into said disposable sensor, and based on qualities of signals received from said pre-selected portions, the microprocessor being programmed with instructions to determine a selected region in said at least one pre-selected pattern of analyte-specific receptors to subsequently monitor said diffracted light signals after sample has been admitted into said disposable vessel;
    said microprocessor controller also being connected to
        said temperature controller, and programmed to control the temperature controller to control the temperature in said analyzer,
        said robotic manipulator, and programmed to pre-position said fluid holding sample container with respect to said fluid dispenser,
        said fluid flow and handling system, and programmed to control sample and assay fluid flow routes through said fluid control system,
        said optical system, and programmed to control parameters of said coherent light beam, said optical detector being configured to analyze said measured diffracted light signals from said at least one pre-selected pattern of analyte-specific receptors for determining a presence or absence of analytes in said sample based on the presence or absence of a change in diffraction pattern before and after sample has been admitted into said disposable vessel; and said microprocessor controller including a user interface enabling interaction between the analyzer and an operator.

2. The analyzer according to claim 1 wherein said disposable sensor includes an integrally formed optical element configured to direct said coherent beam of light towards said surface of said at least one sample well.

3. The analyzer according to claim 1 wherein said at least one sensor station includes a sensor receiving structure matching a form fit of the disposable sensor and having contact surfaces for contacting associated surfaces on said disposable sensor, said contact surfaces being configured to provide positional locationing of the optical element in the at least one sensor station at a location in closest proximity to selected optical surfaces of said optical element to provide optical alignment of the disposable sensor in the at least one sensor station and at the same time providing thermal contact between the sensor receiving structure and the disposable sensor at a location close to the pre-selected patterns and the at least one sample well in the disposable sensor.

4. The analyzer according to claim 1 wherein said optical system is mounted on a rigid optical support structure, a coherent light source for producing said coherent beam of light being rigidly mounted to said rigid optical support structure, said optical detector being rigidly mounted to said rigid optical support structure in a fixed orientation with respect to said coherent light source, and wherein said scanning mechanism includes a motor connected to said rigid optical support structure for moving said rigid optical support structure with respect to said at least one sensor station.

5. The analyzer according to claim 4 wherein said rigid optical support structure is a unitary metal block assembly having bores machined therein, a first bore having a size selected to hold said source of coherent light, a second bore having a size selected to hold said first optical detector, said source of coherent light and said optical detector being in thermal contact with said unitary metal block assembly to provide a stable thermal relationship between said coherent light source and said optical detector.

6. The analyzer according to claim 5 wherein said at least one sensor station forms part of a frame assembly, and wherein said motor is rigidly attached to said frame assembly, and wherein said scanning mechanism includes a ball screw coupled to said motor, said ball screw being mounted so it is axially static with respect to said frame assembly, and wherein said ball screw is connected to said block assembly whereby rotation of the ball screw is translated into linear motion of said unitary metal block assembly in a longitudinal direction.

7. The analyzer according to claim 6 wherein said optical system includes a second optical detector configured to measure reflected light signals from said at least one pre-selected pattern of analyte-specific receptors, and wherein said second optical detector is mounted in a third bore located in said unitary metal block assembly.

8. The analyzer according to claim 7 wherein said microprocessor controller is configured to compare said diffracted light signals captured by the first optical detector and said reflected light signals captured by the second optical detector for purposes of calibration.

9. The analyzer according to claim 6 wherein said temperature controller is configured to maintain a temperature of said unitary metal block assembly at a fixed temperature above ambient in order to stabilize the electronics of the source of coherent light and said first detector and to minimize the affects of thermal gradients induced by changes in the ambient temperature of the operating environment of the analyzer.

10. The analyzer according to claim 6 wherein said rigid unitary metal block assembly is slidably attached to said at least one sensor station wherein upon activation of said motor said rigid optical support structure slides in said longitudinal direction with respect to said at least one sensor station.

11. The analyzer according to claim 10 wherein said rigid optical support structure is slidably attached using at least one rail connected to said rigid optical support structure which is captured by rail receiving means associated with said at least one sensor station.

12. The analyzer according to claim 10 wherein said at least one disposable sensor is elongate having a longitudinal direction, and wherein said at least one preselected pattern of analyte-specific receptors is two or more preselected patterns arrayed along said longitudinal direction so that as said scanning mechanism slides said rigid optical support structure in said longitudinal direction with respect to said at least one sensor station, each of said two or more pre-selected analyte-receptor patterns are presented to the coherent light beam.

13. The analyzer according to claim 12 wherein said at least one disposable sensor is two or more disposable sensors aligned in said longitudinal direction, such that each of the pre-selected analyte-receptor patterns in each of the two or more disposable sensors are presented to the coherent light beam.

14. The analyzer according to claim 12 wherein said microprocessor controller is configured to present any of the at least one pre-selected analyte-receptor patterns in said at least one disposable sensor to the coherent light beam in any order.

15. The analyzer according to claim 6 wherein said scanning mechanism includes a home switch and a limit switch to provide a positional reference and travel limit, respectively, for the unitary metal block assembly, said home switch and said limit switch being connected to said microprocessor controller for providing feedback on location of the unitary metal block.

16. The analyzer according to claim 1 wherein said coherent beam of light is a laser beam.

17. The analyzer according to claim 16 wherein said a laser beam has a wavelength in a red portion of the optical spectrum.

18. The analyzer according to claim 7 wherein said second optical detector is a pre-amplified photodiode package.

19. The analyzer according to claim 1 wherein said first optical detector is a pre-amplified photodiode package.

20. The analyzer according to claim 1 wherein said coherent beam of light has a cross sectional beam size less than an area of the pre-selected pattern of analyte-specific receptors.

21. The analyzer according to claim 1 including a cover lid for covering each of the at least one disposable sensors in each of said at least one sensor stations during operation, including a microprocessor controlled interlock connected to each cover lid and said microprocessor controller is configured so that said beam of coherent light is not turned on unless the interlock is engaged by the cover lid being locked in a closed position.

22. The analyzer according to claim 1 wherein said fluid flow and handling system includes a multi-channel electronic pipetting system.

23. The analyzer according to claim 1 wherein said fluid flow and handling system includes disposable pipette tips.

24. The analyzer according to claim 1 wherein said fluid flow and handling system includes a tip washing station.

25. The analyzer according to claim 1 wherein said integrally formed optical element configured to direct said coherent beam of light towards said surface of said at least one sample well has a geometric shape configured such that the beam of coherent light undergoes total internal reflection in said disposable sensor as the beam of coherent light interacts with said at least one pre-selected pattern of analyte-specific receptors bound to said surface of said at least one sample well.

26. The analyzer according to claim 1 wherein said disposable sensor includes a molded plastic bottom section having a fluid well having an inner surface to which said at least one pre-selected pattern of analyte-specific receptors are bound, a molded plastic lid insertable into said first molded plastic section which when the molded plastic lid is assembled with the molded plastic bottom section defines an interior chamber to allow flow of liquid across the at least one pre-selected pattern of analyte-receptor patterns, said molded plastic lid including an inlet port and an outlet port and flexible tubes each coupled at one end thereof to said inlet and outlet ports and the other ends of each flexible tube being connected to fluidic connectors which are releasibly connectable to said fluid flow and handling system.

27. The analyzer according to claim 1 wherein the microprocessor is programmed with instructions such that at a time that a fluid containing a reactive species contacts a monitored region of the at least one pre-selected pattern of analyte-specific receptors the microprocessor identifies a diffraction signal change induced by an intentional introduction into the at least one sample well of a fluid differing in refractive index from the fluid containing the reactive species immediately prior to introduction of the fluid containing the reactive species into said at least one sample well.

28. The analyzer according to claim 1 wherein the microprocessor is programmed with instructions such that a location of the analyte-receptor pattern is identified and aligned to the optical system by comparing pattern scan data of a scanned pattern to a theoretical pattern and a map of the analyte-receptor pattern location relative to the optical system is produced.

29. The analyzer according to claim 28 wherein the microprocessor is programmed with instructions such that said scanned pattern is matched in software to the theoretical pattern and locational references in the system software are adjusted accordingly.

30. The analyzer according to claim 29 wherein the microprocessor is programmed with instructions such that said matching of the expected signal pattern to the actual pattern measured by the optical system is accomplished by applying a lowest-quartile-filter to said actual pattern thus establishing a location of actual expected regions of low signal between the analyte-receptor patterns, and cross correlating this actual pattern to the expected pattern and the locational references in appropriate software files.

31. The analyzer according to claim 1 wherein the microprocessor is programmed with instructions such that said selected region in said at least one pre-selected pattern of analyte-specific receptors is selected by comparing signal amplitudes in adjacent regions and selecting a region with least deviation from a local or distributed signal level.

32. The analyzer according to claim 1 wherein the microprocessor is programmed with instructions such that said selected region in said at least one pre-selected pattern of analyte-specific receptors is selected by restriction to regions of pre-selected signal intensity.

33. The analyzer according to claim 1 wherein the microprocessor is programmed with instructions such that said selected region in said at least one pre-selected pattern of analyte-specific receptors is selected by exclusion of regions above a signal intensity which limits analytical dynamic range.

34. The analyzer according to claim 1 wherein the microprocessor is programmed with instructions such that said selected region in said at least one pre-selected pattern of analyte-specific receptors is selected by exclusion of regions below a signal intensity which corresponds to an incomplete pattern.

* * * * *